United States Patent
Shigemori

(10) Patent No.: US 8,419,618 B2
(45) Date of Patent: Apr. 16, 2013

(54) DISPLAY DEVICE AND IN-VIVO INFORMATION ACQUIRING SYSTEM USING THE SAME

(75) Inventor: Toshiaki Shigemori, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 925 days.

(21) Appl. No.: 12/535,273

(22) Filed: Aug. 4, 2009

(65) Prior Publication Data
US 2009/0292174 A1 Nov. 26, 2009

Related U.S. Application Data

(63) Continuation of application No. PCT/JP2008/051847, filed on Feb. 5, 2008.

(30) Foreign Application Priority Data

Feb. 5, 2007 (JP) ................................. 2007-025894

(51) Int. Cl.
*A61B 1/00* (2006.01)
*A61B 5/07* (2006.01)

(52) U.S. Cl.
USPC ........................................ 600/117; 600/302

(58) Field of Classification Search .................. 600/109, 600/117–118, 302
See application file for complete search history.

(56) References Cited

U.S. PATENT DOCUMENTS

| | | | |
|---|---|---|---|
| 6,904,308 B2 | 6/2005 | Frisch et al. | |
| 8,100,888 B2* | 1/2012 | Segawa et al. | 604/890.1 |
| 2004/0181127 A1 | 9/2004 | Matsumoto et al. | |
| 2007/0221233 A1* | 9/2007 | Kawano et al. | 600/160 |
| 2008/0097149 A1* | 4/2008 | Adler et al. | 600/109 |
| 2008/0249359 A1* | 10/2008 | Abraham-Fuchs et al. | 600/117 |
| 2010/0268026 A1* | 10/2010 | Takizawa | 600/109 |
| 2012/0203068 A1* | 8/2012 | Sato et al. | 600/117 |

FOREIGN PATENT DOCUMENTS

| | | |
|---|---|---|
| JP | 07-213515 | 8/1995 |
| JP | 2003-19111 | 1/2003 |
| JP | 2003-116781 A | 4/2003 |
| JP | 2004-298560 | 10/2004 |
| JP | 2005-110943 | 4/2005 |
| JP | 2005-124756 A | 5/2005 |
| JP | 2005-131012 | 5/2005 |
| JP | 2005-185644 | 7/2005 |
| JP | 2005-218584 A | 8/2005 |
| WO | WO 2007/077895 A1 | 7/2007 |

OTHER PUBLICATIONS

Machine translation of JP2004-298560.*
Machine translation of JP2004-298560 published Oct. 28, 2004.*

(Continued)

*Primary Examiner* — Christopher Mahoney
(74) *Attorney, Agent, or Firm* — Scully Scott Murphy & Presser, PC

(57) ABSTRACT

A display device includes: a display unit that displays examination procedure information indicating an examination procedure of a subject; and a control unit that acquires position-related information of a capsule endoscope inserted into the subject, calculates a position of the capsule endoscope based on the acquired position-related information, determines a to-be-executed examination procedure of the subject corresponding to the calculated position, and performs control to display the examination procedure information indicating the determined to-be-executed examination procedure of the subject.

13 Claims, 22 Drawing Sheets

OTHER PUBLICATIONS

Japanese Office Action dated Jul. 31, 2012 from corresponding Japanese Patent Application No. 2008-557114 together with an English language translation.

Japanese Office Action dated May 8, 2012 from corresponding Japanese Patent Application No. 2008-557114.

* cited by examiner

FIG.18

| POSTURE OF SUBJECT | LEG LENGTH OF BED | | | |
|---|---|---|---|---|
| | RIGHT FRONT LEG | LEFT FRONT LEG | RIGHT REAR LEG | LEFT REAR LEG |
| TRENDELENBURG'S POSITION | L/2 | L/2 | L | L |
| LEFT LATERAL DECUBITUS POSITION | L | L/2 | L | L/2 |
| SITTING POSITION | L | L | L/2 | L/2 |

DISPLAY DEVICE AND IN-VIVO INFORMATION ACQUIRING SYSTEM USING THE SAME

CROSS-REFERENCE TO RELATED APPLICATIONS

This application is a continuation of PCT international application Ser. No. PCT/JP2008/051847 filed on Feb. 5, 2008 which designates the United States, incorporated herein by reference, and which claims the benefit of priority from Japanese Patent Application No. 2007-025894, filed on Feb. 5, 2007, incorporated herein by reference.

BACKGROUND OF THE INVENTION

1. Field of the Invention

The present invention relates to a display device that acquires images of inside of internal organs (an example of in-vivo information) captured by a capsule endoscope inserted into internal organs of a subject such as a patient and displays the acquired image of inside of the internal organs, and relates to an in-vivo information acquiring system using the same.

2. Description of the Related Art

Conventionally, in the field of endoscope, a swallow-type capsule endoscope having an imaging function and a wireless communication function has been proposed, and an in-vivo information acquiring system has been developed, which acquires an image group of inside of internal organs captured by a capsule endoscope inserted into internal organs of a subject such as a patient. In such an in-vivo information acquiring system, a capsule endoscope is swallowed from a mouth of a subject for observation (examination) of internal organs. The capsule endoscope then advances in the internal organs such as esophagus, stomach, and small intestine with peristaltic movements until it is naturally excreted from the subject, while sequentially capturing images of the inside of the internal organs of the subject (hereinafter, also referred to as "in-vivo images"), for example, at 0.5-second intervals along time series.

A receiving device of the in-vivo information acquiring system is carried by the subject, into which the capsule endoscope is inserted, and receives an image group of inside of the internal organs wirelessly transmitted by the capsule endoscope in the subject. A portable storage medium is detachably attached to the receiving device, and the image group of the inside of the internal organs received from the capsule endoscope is sequentially stored in the storage medium.

After the capsule endoscope is naturally excreted from the subject, a user such as a doctor or nurse records the image group of the inside of the internal organs stored in the storage medium of the receiving device into a display device. A display device of the in-vivo information acquiring system displays the image group of the inside of the internal organs acquired via the storage medium on a display. The user can observe in-vivo images sequentially displayed on the display of the display device to diagnose the subject (For example, see Japanese Patent Application Laid-open No. 2003-19111).

SUMMARY OF THE INVENTION

A display device according to an aspect of the present invention includes: a display unit that displays examination procedure information indicating an examination procedure of a subject; and a control unit that acquires position-related information of a capsule endoscope inserted into the subject, calculates a position of the capsule endoscope based on the acquired position-related information, determines a to-be-executed examination procedure of the subject corresponding to the calculated position, and performs control to display the examination procedure information indicating the determined to-be-executed examination procedure of the subject.

An in-vivo information acquiring system according to another aspect of the present invention includes: a mounting unit that has a subject mounted thereon; a driving unit that drives the mounting unit to change a posture of the subject; a receiver that receives in-vivo images captured by a capsule endoscope inserted into the subject and position-related information of the capsule endoscope; and a display device that acquires the in-vivo images and displays the acquired in-vivo images, wherein the display device includes a control unit that acquires the position-related information, calculates a position of the capsule endoscope based on the acquired position-related information, determines a posture to be taken by the subject corresponding to the calculated position, and performs drive control of the driving unit to change the posture of the subject according to the determined posture to be taken by the subject.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 18 is a schematic diagram of an example of pieces of leg length data of a bed corresponding to a posture to be taken by a subject;

DETAILED DESCRIPTION OF THE PREFERRED EMBODIMENTS

Exemplary embodiments of a display device and an in-vivo information acquiring system using the same according to the present invention will be described below in detail with reference to the accompanying drawings. A case that a capsule endoscope is inserted into a subject to acquire an image group of inside of large intestine of the subject is exemplified to explain embodiments of the display device and the in-vivo information acquiring system using the same according to the present invention. However, the present invention is not limited to the embodiments.

First Embodiment

Figure 1:
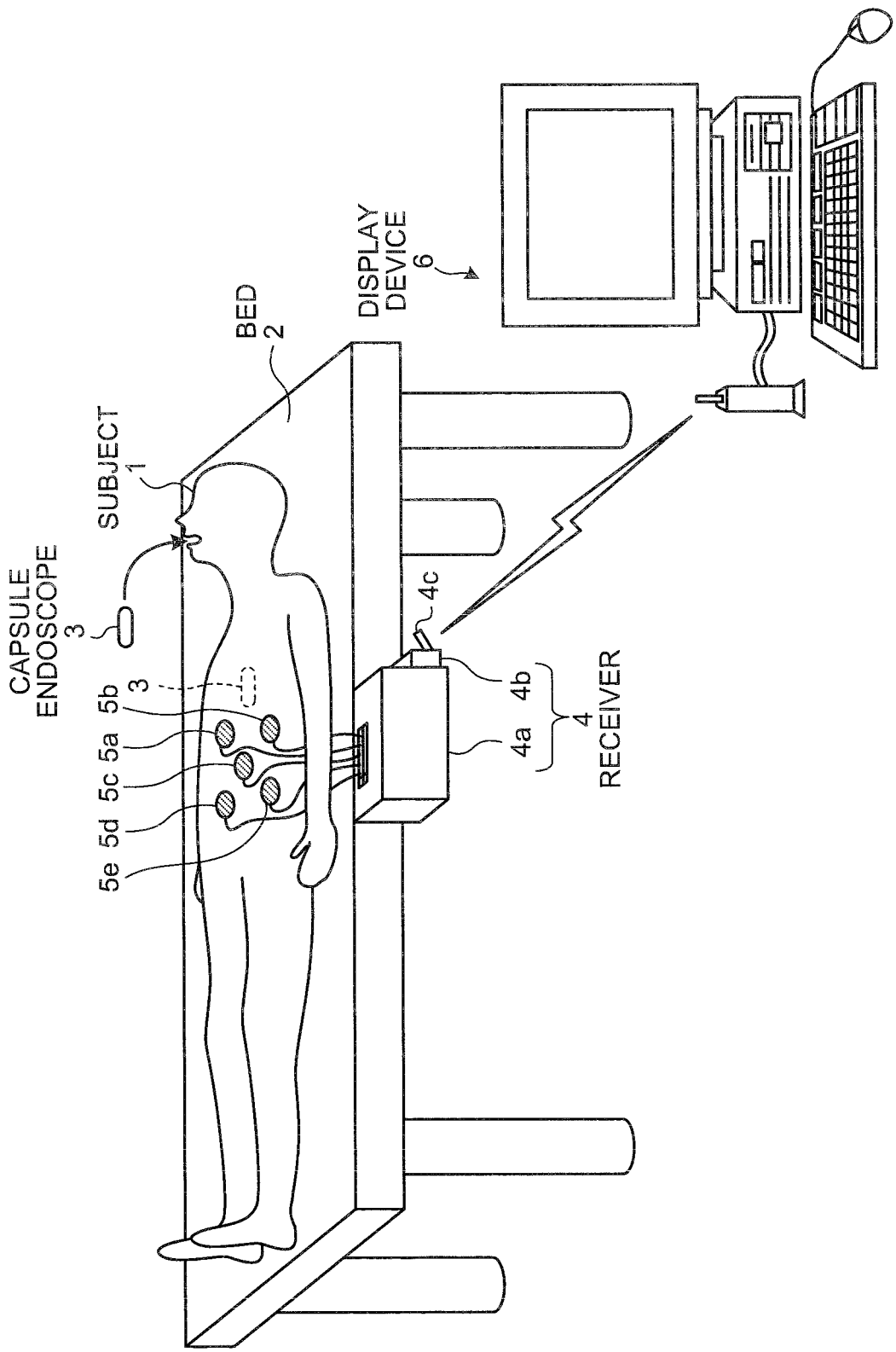
FIG. 1 is a schematic diagram of a configuration example of an in-vivo information acquiring system according to a first embodiment of the present invention.

FIG. 1 is a schematic diagram of a configuration example of an in-vivo information acquiring system according to a first embodiment of the present invention. As shown in FIG. 1, the in-vivo information acquiring system according to the first embodiment includes a capsule endoscope 3 that captures in-vivo images of a subject 1 such as a patient, a receiver 4 that receives the in-vivo images and the like of inside of internal organs of the subject 1 captured by the capsule endoscope 3, and a display device 6 that displays the in-vivo images and the like received by the receiver 4.

The capsule endoscope 3 is inserted into the subject 1 for capturing images of inside of a desired internal organ (for example, inside of large intestine) in the subject 1. The capsule endoscope 3 has an imaging function for capturing the in-vivo images of the subject 1, a wireless communication function for wirelessly transmitting image signals corresponding to the captured in-vivo images, and a battery for supplying power to execute the imaging function and the wireless communication function, in a capsule casing that is easily insertable into internal organ of the subject 1. Specifically, the capsule endoscope 3 sequentially advances in an internal organ with peristaltic movements of the internal organs after being swallowed from a mouth of the subject 1. Simultaneously therewith, the capsule endoscope 3 sequentially captures the in-vivo images of the subject 1 at predetermined intervals (for example, 0.5-second intervals) by consuming the power of the battery, and sequentially wirelessly transmits the image signals corresponding to captured in-vivo images to the external receiver 4.

The receiver 4 is installed, for example, on a bed 2 that has the subject 1 mounted thereon, receives the in-vivo images of internal organs of the subject 1 captured by the capsule endoscope 3, and transmits various pieces of information such as the in-vivo images to the display device 6. The receiver 4 includes a receiver main unit 4a and a communication unit 4b.

The receiver main unit 4a includes plural receiving antennas 5a to 5e distributed on a body surface of the subject 1, and receives image signals from the capsule endoscope 3 inside the internal organs of the subject 1 via these receiving antennas 5a to 5e. Simultaneously therewith, the receiver main unit 4a acquires received field strength (hereinafter, referred to as "received field strength information") for each receiving antennas 5a to 5e at the time of receiving the image signals. The receiver main unit 4a performs demodulation processing with respect to the image signal to acquire the in-vivo image corresponding to the image signal. The receiver main unit 4a sequentially transmits the in-vivo images and the received field strength information associated with each in-vivo image to the communication unit 4b.

The communication unit 4b transmits the in-vivo image and the received field strength information associated with each other by the receiver main unit 4a to the display device 6. Specifically, the communication unit 4b includes an antenna 4c for performing wireless communication with the display device 6 and is connected to the receiver main unit 4a. The communication unit 4b acquires the in-vivo image and the received field strength information associated with each other by the receiver main unit 4a from the receiver main unit 4a to generate a wireless signal including the acquired in-vivo image and received field strength information. The communication unit 4b transmits the wireless signal including the in-vivo image and the received field strength information to the display device 6 via the antenna 4c.

The receiving antennas of the receiver 4 exemplified by the receiving antennas 5a to 5e need only to be arranged on the body surface of the subject 1 so that image signals wirelessly transmitted from the capsule endoscope 3 inserted into the internal organs of the subject 1 can be received. Therefore, for example, when the internal organ to be observed is large intestine, the receiving antennas can be arranged on a body surface near large intestine. The number of receiving antennas to be arranged can be at least one, and is not limited to five.

The display device 6 displays various images such as the in-vivo images of the subject 1 captured by the capsule endoscope 3. Specifically, the display device 6 performs wireless communication with the communication unit 4b in the receiver 4, and has a configuration of, for example, a workstation that displays various pieces of information such as the in-vivo images of the subject 1 based on the various pieces of information acquired by the wireless communication. As the various pieces of information displayed by the display device 6, there can be mentioned the in-vivo images of the subject 1 captured by the capsule endoscope 3, a position image indicating a reached position in the internal organ where the capsule endoscope 3 has reached, and a posture image indicating a posture to be taken by the subject 1 who has the capsule endoscope 3 in his internal organs. The display device 6 has a processing function for observing (examining) the in-vivo images of the subject 1 to diagnose the subject 1 by a user such as a doctor or nurse. In this case, the user has the display device 6 sequentially displayed the in-vivo images of the subject 1 to observe (examine) inside of an internal organ such as esophagus, stomach, small intestine, and large intestine of the subject 1, and can diagnose the subject 1 based on the observation result.

Figure 2:
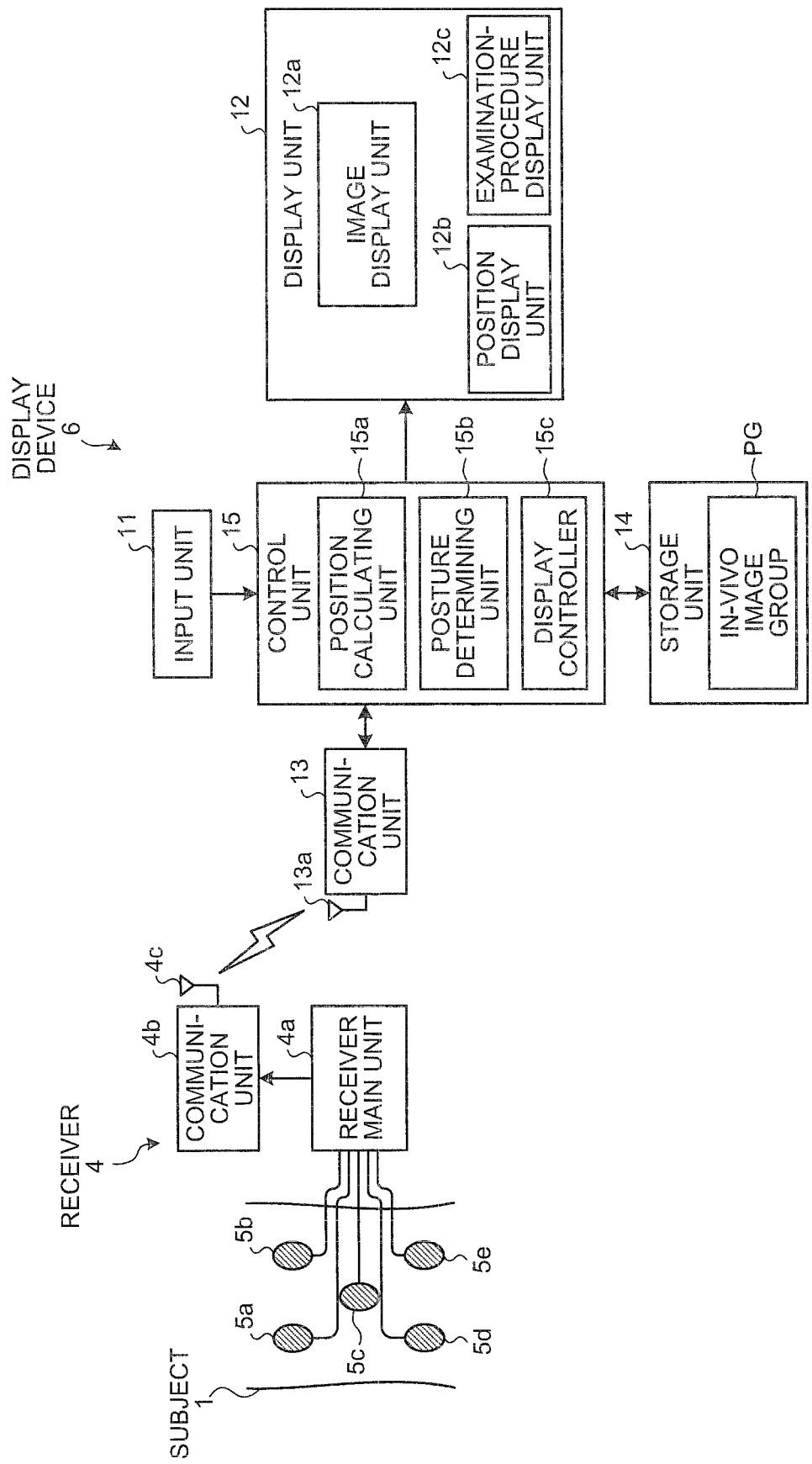
FIG. 2 is a block diagram for schematically depicting a configuration example of a display device according to the first embodiment of the present invention.

The configuration of the display device 6 according to the first embodiment of the present invention will be described next. FIG. 2 is a block diagram schematically depicting a configuration example of the display device 6 according to the first embodiment of the present invention. In FIG. 2, the receiver 4 that wirelessly transmits the various pieces of information such as the in-vivo images of the subject 1 and the received field strength information to the display device 6 is shown as well.

As shown in FIG. 2, the display device 6 according to the first embodiment includes an input unit 11 that inputs various pieces of information, a display unit 12 that displays various pieces of information such as in-vivo images of the subject 1, and a communication unit 13 that performs the wireless communication with the receiver 4. The display device 6 also includes a storage unit 14 that stores various pieces of information such as the in-vivo images of the subject 1, and a control unit 15 that controls respective components of the display device 6.

The input unit 11 is embodied by using an input device such as a keyboard and a mouse, and inputs various pieces of information to the control unit 15 in response to an input operation by a user. The various pieces of information input to the control unit 15 by the input unit 11 include, for example, various pieces of instruction information for instructing the control unit 15, and patient information relating to the subject 1 such as patient name, sex, date of birth, and patient ID of the subject 1.

The display unit 12 is embodied by using a display capable of displaying images such as a CRT display or a liquid crystal display, and displays various pieces of information instructed to be displayed by the control unit 15. Specifically, the display unit 12 includes an image display unit 12a, a position display unit 12b, and an examination-procedure display unit 12c. The image display unit 12a displays the in-vivo images of the subject 1 captured by the capsule endoscope 3. The position display unit 12b displays a position image indicating the reached position in the internal organ where the capsule endoscope 3 in the subject 1 has reached (hereinafter, referred to as "intra-organ reached position"). The examination-procedure display unit 12c displays the posture image indicating a posture to be taken by the subject 1 who has the capsule endoscope 3 in his internal organ. The display unit 12 having the examination-procedure display unit 12c functions as a display unit that displays posture information, for example, indicating the posture to be taken by the subject 1 on the bed 2. The position image displayed by the position display unit 12b is an example of the position information indicating the intra-organ reached position, and the posture image displayed by the examination-procedure display unit 12c is an example of the posture information indicating the posture to be taken by the subject 1. Further, the posture information is an example of examination procedure information indicating an examination procedure to be performed by the subject 1.

The communication unit 13 performs wireless communication with the communication unit 4b of the receiver 4 to acquire the in-vivo images and the received field strength information from the receiver 4. Specifically, the communication unit 13 includes an antenna 13a to sequentially receive wireless signals transmitted from the communication unit 4b of the receiver 4 via the antenna 13a. Each time upon reception of the wireless signals from the receiver 4, the communication unit 13 performs demodulation processing with respect to the wireless signals to acquire the in-vivo images of the subject 1 and the received field strength information included in the wireless signals. The communication unit 13 sequentially transmits the acquired in-vivo images of the subject 1 and the received field strength information to the control unit 15.

The storage unit 14 is embodied by using a large-capacity storage medium such as RAM, EEPROM, or hard disk, and stores various pieces of information instructed to store by the control unit 15 and transmits stored information instructed to be read by the control unit 15 to the control unit 15. Specifically, the storage unit 14 stores an in-vivo image group PG of the subject 1 acquired by the control unit 15 via the communication unit 13. The storage unit 14 also stores the respective pieces of received field strength information associated with the in-vivo images in the in-vivo image group PG.

The control unit 15 controls the respective components of the display device 6. Specifically, the control unit 15 controls each of the input unit 11, the display unit 12, the communication unit 13, and the storage unit 14, and controls input and output of information between the respective components. The control unit 15 also controls wireless communication operation of the communication unit 13, and acquires the in-vivo image group PG of the subject 1 and the received field strength information of each in-vivo image via the communication unit 13. The control unit 15 stores the thus acquired in-vivo image group PG and respective pieces of received field strength information in the storage unit 14. The control unit 15 controls the image display unit 12a to sequentially display the respective in-vivo images in the in-vivo image group PG based on instruction information input by the input unit 11. The control unit 15 further controls the position display unit 12b in the display unit 12 to display a position image indicating the intra-organ reached position where the capsule endoscope 3 inside the subject 1 has reached, and controls the examination-procedure display unit 12c in the display unit 12 to display a posture image indicating a posture to be taken by the subject who has the capsule endoscope 3 in his internal organ, which has reached the intra-organ reached position.

The control unit 15 includes a position calculating unit 15a, a posture determining unit 15b, and a display controller 15c. The position calculating unit 15a calculates a position of the capsule endoscope 3 (hereinafter, referred to as "capsule position") based on the received field strength information, which is an example of position-related information of the capsule endoscope 3 inserted into the internal organ of the subject 1. Specifically, the position calculating unit 15a calculates the capsule position at the time of capturing the in-vivo image based on the received field strength of the respective receiving antennas 5a to 5e when the in-vivo image in the in-vivo image group PG is received via the receiving antennas 5a to 5e. In this case, the received field strength information is an example of information relating to a position of the capsule endoscope 3 in the subject 1. The position calculating unit 15a calculates the intra-organ reached position of the capsule endoscope 3 at the time of capturing the in-vivo image, based on the capsule position when the in-vivo image is captured, and specifies the intra-organ reached position corresponding to the in-vivo image and the capsule position.

The posture determining unit 15b determines the posture to be taken by the subject 1 corresponding to the capsule position calculated by the position calculating unit 15a. Specifically, the posture determining unit 15b includes plural pieces of posture information indicating the posture to be taken by the subject 1 for accelerating the advancement of the capsule endoscope 3 in the internal organs for each intra-organ reached position of the capsule endoscope 3. The posture determining unit 15b determines the posture of the subject 1 corresponding to the intra-organ reached position specified by the position calculating unit 15a from among the pieces of posture information, and determines the posture to be taken by the subject 1 who has the capsule endoscope 3 in his internal organ, which has reached the intra-organ reached position. Specifically, when an observed region of the subject 1 is large intestine, the posture determining unit 15b has plural postures (Trendelenburg's position, left lateral decubitus position, sitting position, and the like) for each reached position in the large intestine (ascending colon, transverse colon, descending colon, and the like).

The Trendelenburg's position of these postures is an example of the posture to be taken by the subject 1 for accelerating the advancement of the capsule endoscope 3 having reached the ascending colon. The left lateral decubitus position of these postures is an example of the posture to be taken by the subject 1 for accelerating the advancement of the capsule endoscope 3 having reached the transverse colon. The sitting position of these postures is an example of the posture to be taken by the subject 1 for accelerating the advancement of the capsule endoscope 3 having reached the descending colon.

The display controller 15c performs control to display various images on the display unit 12. Specifically, the display controller 15c performs control to sequentially display the respective in-vivo images of the subject 1 included in the in-vivo image group PG on the image display unit 12a. The display controller 15c further performs control to display the position image indicating the intra-organ reached position of the capsule endoscope 3 calculated by the position calculating unit 15a on the position display unit 12b. The display controller 15c also performs control to display the posture image indicating the posture to be taken by the subject 1 determined by the posture determining unit 15b on the examination-procedure display unit 12c.

Figure 3:
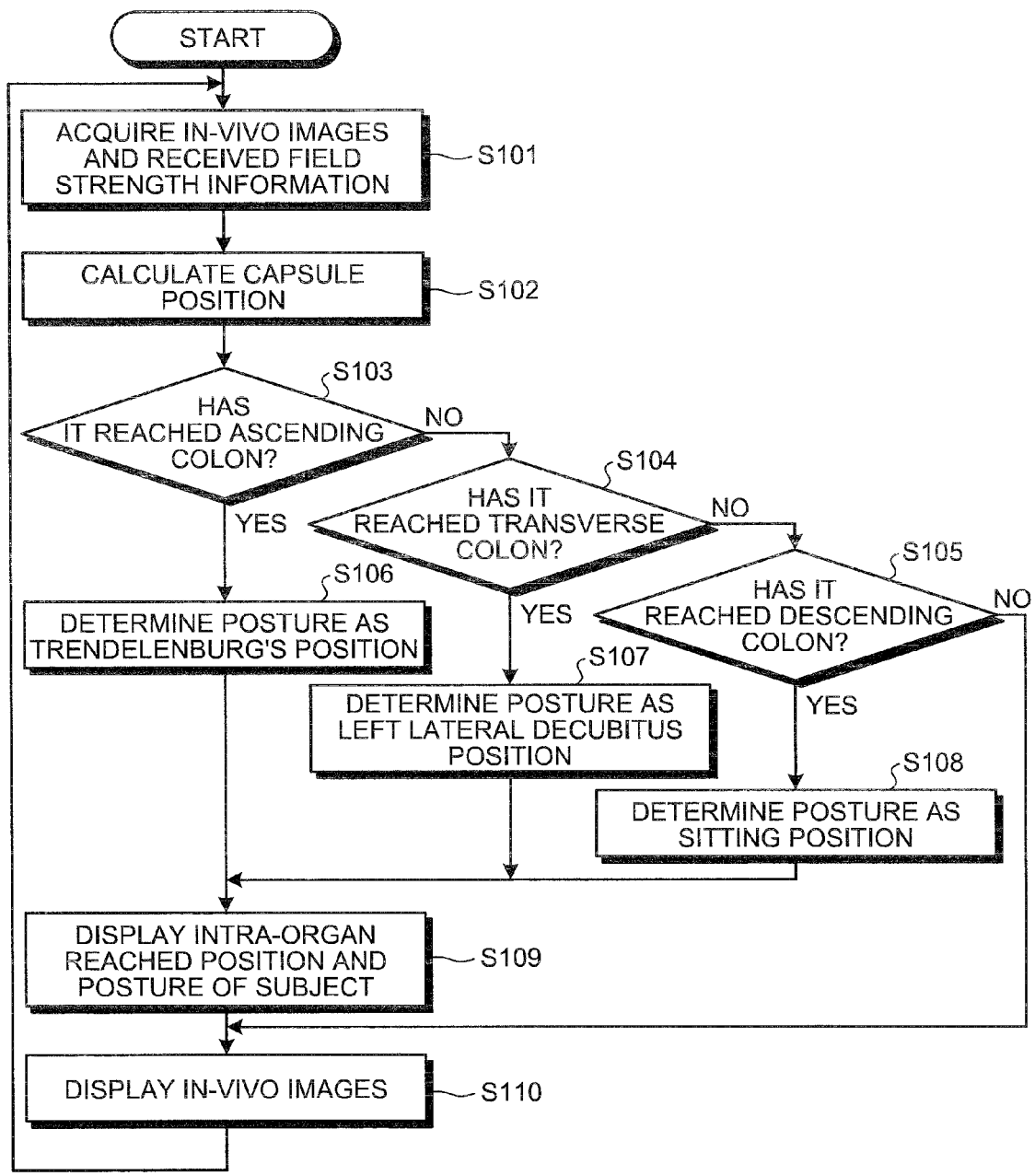
FIG. 3 is a flowchart for exemplifying a process procedure performed by a control unit of the display device according to the first embodiment of the present invention.

An operation of the control unit 15 in the display device 6 according to the first embodiment of the present invention will be described next. FIG. 3 is a flowchart for exemplifying a process procedure performed by the control unit 15 in the display device 6 according to the first embodiment of the present invention. When the capsule endoscope 3 inserted into the internal organs of the subject 1 has reached large intestine (an example of observed region), the control unit 15 performs control to display the posture to be taken by the subject 1 corresponding to the intra-organ reached position (ascending colon, transverse colon, or descending colon) of the capsule endoscope 3 on the display unit 12.

That is, as shown in FIG. 3, the control unit 15 acquires the in-vivo images of the subject 1 and the received field strength information (Step S101). Specifically, the control unit 15 acquires the in-vivo images of the subject 1 via the communication unit 13 and also acquires received field strength for each receiving antenna included in the received field strength information corresponding to the in-vivo images. The received field strength for each receiving antenna is received field strength of each of the receiving antennas 5a to 5e when the in-vivo images are received via the receiving antennas 5a to 5e. The control unit 15 stores the acquired in-vivo images and the received field strength information in the storage unit 14.

The control unit 15 calculates the capsule position based on the received field strength acquired at Step S101 (Step S102). In this case, the position calculating unit 15a calculates the capsule position based on a difference in the received field strength of each receiving antenna included in the received field strength information acquired at Step S101. Specifically, the position calculating unit 15a calculates the capsule position at the time of capturing the in-vivo images, based on the difference in the received field strength of each receiving antenna 5a to 5e when the in-vivo images acquired at Step S101 are received via the receiving antennas 5a to 5e.

The capsule position calculated by the position calculating unit 15a is a relative position with respect to the receiving antennas 5a to 5e distributed on the body surface of the subject 1. Accordingly, the position calculating unit 15a calculates respective relative distances of the capsule endoscope 3 with respect to the receiving antennas 5a to 5e by using the received field strength, thereby enabling to calculate the capsule position based on trilateration or the like using the respective relative distances.

Thereafter, the control unit 15 determines whether the capsule endoscope 3 in the subject 1 has reached the predetermined intra-organ reached position (that is, a position in large intestine, which is an organ to be observed). Specifically, the control unit 15 determines whether the capsule endoscope 3 is in a state of having reached the ascending colon (Step S103). When determining that the capsule endoscope 3 is not in this state (No at Step S103), the control unit 15 determines whether the capsule endoscope 3 is in a state of having reached the transverse colon (Step S104). When determining that the capsule endoscope 3 is not in this state (No at Step S104), the control unit 15 determines whether the capsule endoscope 3 is in a state of having reached the descending colon (Step S105).

At Steps S103 to S105, the position calculating unit 15a calculates the intra-organ reached position of the capsule endoscope 3 corresponding to the capsule position, based on the relative positions of the capsule endoscope 3 with respect to the receiving antennas 5a to 5e distributed on the body surface of the subject 1, that is, the capsule position calculated at Step S102. If the intra-organ reached position calculated by the position calculating unit 15a is not in the ascending colon of the subject 1, the control unit 15 determines that the capsule endoscope 3 is not in the state of having reached the ascending colon. If the intra-organ reached position is not in the transverse colon of the subject 1, the control unit 15 determines that the capsule endoscope 3 is not in the state of having reached the transverse colon. Further, if the intra-organ reached position is not in the descending colon of the subject 1, the control unit 15 determines that the capsule endoscope 3 is not in the state of having reached the descending colon.

On the other hand, at Step S103, if the intra-organ reached position calculated by the position calculating unit 15a is in the ascending colon of the subject 1, the control unit 15 determines that the capsule endoscope 3 is in the state of having reached the ascending colon (Yes at Step S103), and sets the posture to be taken by the subject 1, who has the capsule endoscope 3 in his internal organ (that is, ascending colon), as the Trendelenburg's position (Step S106). In this case, the posture determining unit 15b determines the posture of the subject 1 corresponding to the ascending colon, which is the intra-organ reached position specified by the position calculating unit 15a, from among the preset pieces of posture information, and when the capsule endoscope 3 has reached the inside of the ascending colon, sets the posture to be taken by the subject 1 as the Trendelenburg's position.

At Step S104, if the intra-organ reached position calculated by the position calculating unit 15a is in the transverse colon of the subject 1, the control unit 15 determines that the capsule endoscope 3 is in the state of having reached the transverse colon (Yes at Step S104), and sets the posture to be taken by the subject 1, who has the capsule endoscope 3 in his internal organ (that is, transverse colon), as the left lateral decubitus position (Step S107). In this case, the posture determining unit 15b determines the posture of the subject 1 corresponding to the transverse colon, which is the intra-organ reached position specified by the position calculating unit 15a, from among the preset pieces of posture information, and when the capsule endoscope 3 has reached the inside of the transverse colon, sets the posture to be taken by the subject 1 as the left lateral decubitus position.

On the other hand, at Step S105, if the intra-organ reached position calculated by the position calculating unit 15a is in the descending colon of the subject 1, the control unit 15 determines that the capsule endoscope 3 is in the state of having reached the descending colon (Yes at Step S105), and sets the posture to be taken by the subject 1, who has the capsule endoscope 3 in his internal organ (that is, descending colon), as the sitting position (Step S108). In this case, the posture determining unit 15b determines the posture of the subject 1 corresponding to the descending colon, which is the intra-organ reached position specified by the position calculating unit 15a, from among the preset pieces of posture information, and when the capsule endoscope 3 has reached the inside of the descending colon, sets the posture to be taken by the subject 1 as the sitting position.

After having determined the posture to be taken by the subject 1 by performing any one of the process procedures at Steps S106 to S108, the control unit 15 controls the display unit 12 to display the intra-organ reached position of the capsule endoscope 3 inside the subject 1 and the posture of the subject 1 (Step S109). In this case, the display controller 15c performs control to display a position image indicating the intra-organ reached position calculated by the position calculating unit 15a on the position display unit 12b. Further, the display controller 15c performs control to display a posture image indicating the posture to be taken by the subject 1 determined by the posture determining unit 15b on the examination-procedure display unit 12c.

Specifically, when the intra-organ reached position is in the ascending colon, and the posture to be taken by the subject 1 is the Trendelenburg's position, the display controller 15c performs control to display the position image indicating that the capsule endoscope 3 is in the state of having reached the inside of the ascending colon on the position display unit 12b, and performs control to display the posture image indicating the Trendelenburg's position of the subject 1 on the examination-procedure display unit 12c. On the other hand, when the intra-organ reached position is in the transverse colon, and the posture to be taken by the subject 1 is the left lateral decubitus position, the display controller 15c performs control to display the position image indicating that the capsule endoscope 3 is in the state of having reached the inside of the transverse colon on the position display unit 12b, and performs control to display the posture image indicating the left lateral decubitus position of the subject 1 on the examination-procedure display unit 12c. Meanwhile, when the intra-organ reached position is in the descending colon, and the posture to be taken by the subject 1 is the sitting position, the display controller 15c performs control to display the position image indicating that the capsule endoscope 3 is in the state of having reached the inside of the descending colon on the position display unit 12b, and performs control to display the posture image indicating the sitting position of the subject 1 on the examination-procedure display unit 12c.

Next, the control unit 15 controls the display unit 12 to display the in-vivo images of the subject 1 acquired at Step S101 (Step S110). Specifically, the display controller 15c performs control to display the in-vivo images of the subject 1 acquired at Step S101 (that is, in-vivo images stored in the storage unit 14 at Step S101) on the image display unit 12a. Thereafter, the control unit 15 returns to Step S101 and repeats the process procedures at Step S101 and onwards.

At Step S105 described above, if the intra-organ reached position calculated by the position calculating unit 15a is not in the descending colon of the subject 1, the control unit 15 determines that the capsule endoscope 3 is not in the state of having reached the descending colon (No at Step S105), and proceeds to Step S110 to repeat the process procedures at Step S110 and onwards.

The control unit 15 repeats the process procedures at Steps S101 to S110, every time the in-vivo images of the subject 1 and the received field strength information are acquired via the communication unit 13. The control unit 15 controls the image display unit 12a to display the in-vivo images of the subject 1 on a real-time basis. Further, when the intra-organ reached position of the capsule endoscope 3 that has captured the in-vivo images displayed on the image display unit 12a on a real-time basis is the predetermined reached position (for example, any one of the ascending colon, transverse colon, or descending colon), the control unit 15 controls the position display unit 12b to display a position image indicating the intra-organ reached position, and controls the examination-procedure display unit 12c to display a posture image indicating a posture to be taken by the subject 1 corresponding to the intra-organ reached position.

Figure 4:
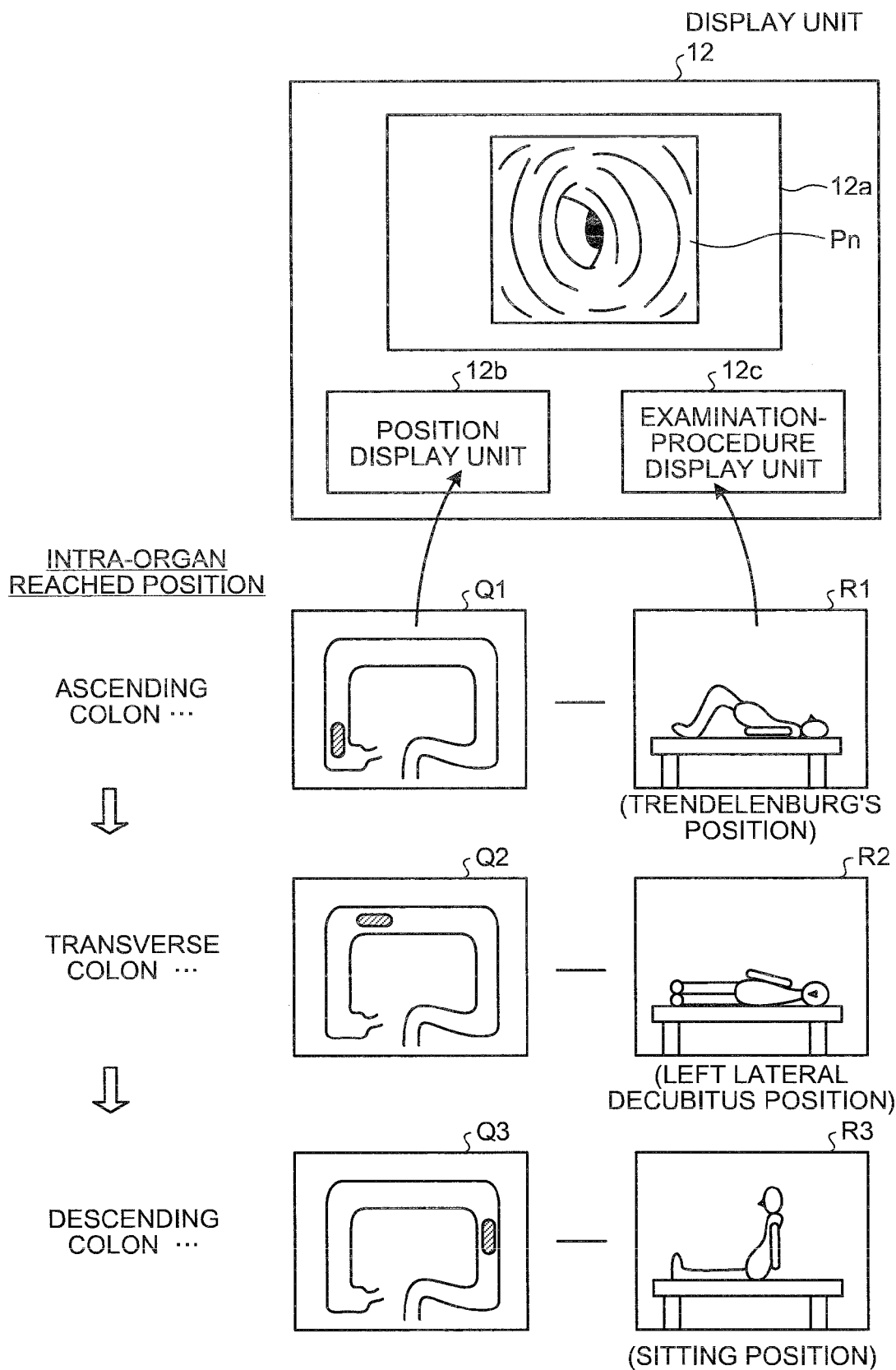
FIG. 4 is a schematic diagram for specifically explaining an operation of the control unit of the display device according to the first embodiment of the present invention.

An operation of the control unit 15 in the display device 6 according to the first embodiment of the present invention will be specifically described next by exemplifying a case that large intestine of the subject 1 is an observed region. FIG. 4 is a schematic diagram for specifically explaining the operation of the control unit 15 in the display device 6 according to the first embodiment of the present invention. The operation of the control unit 15 will be specifically described below with reference to FIG. 4.

The control unit 15 sequentially acquires the in-vivo images of the subject 1 and the received field strength information via the communication unit 13. The capsule endoscope 3 that captures the in-vivo images is swallowed from the mouth of the subject 1, and sequentially passes through the esophagus, stomach, and small intestine with peristaltic movements. While the capsule endoscope 3 sequentially advances inside of the internal organs of the subject 1, the control unit 15 calculates a capsule position at the time of capturing an in-vivo image $P_n$ (frame number n=1, 2, 3, . . . ), based on the received field strength information acquired together with the in-vivo image $P_n$, every time the in-vivo image $P_n$ captured by the capsule endoscope 3 is acquired. The control unit 15 then specifies the intra-organ reached position of the capsule endoscope 3 inside the subject 1 based on the capsule position calculated in this manner, to determine whether the specified intra-organ reached position is at a position inside large intestine (that is, any one of ascending colon, transverse colon, or descending colon).

Until the capsule endoscope 3 in the subject 1 reaches the large intestine, the control unit 15 understands that the intra-organ reached position of the capsule endoscope 3 is not at a position inside the large intestine. In this case, the control unit 15 controls the display unit 12 to sequentially display the in-vivo images $P_n$ captured by the capsule endoscope 3 (in-vivo images of a region other than large intestine such as esophagus, stomach, or small intestine) on a real-time basis, without displaying a position image indicating the intra-organ reached position and a posture image indicating a posture to be taken by the subject 1. A user such as a doctor or nurse can observe the inside of the internal organs of the subject 1 by visually checking the in-vivo images $P_n$ sequentially displayed on the image display unit 12a, and can understand that the capsule endoscope 3 in the subject 1 has not yet reached the large intestine, which is the internal organ to be observed.

When the capsule endoscope has not yet reached the large intestine, the subject 1 takes a posture lying on his/her back on the bed 2 (supine posture), as shown in FIG. 1. It is because the capsule endoscope 3 having reached the inside of a relatively narrow internal organ such as small intestine can easily advance inside the internal organs with peristaltic movements or the like, even when the subject 1 takes the supine posture.

Thereafter, the capsule endoscope 3 inside the subject 1 passes through the inside of the small intestine and reaches ascending colon of the large intestine. When the capsule endoscope 3 has reached the ascending colon, the control unit 15 understands that the intra-organ reached position of the capsule endoscope 3 is in the ascending colon based on the received field strength information acquired together with the in-vivo images $P_n$ captured by the capsule endoscope 3 in the ascending colon. In this case, the control unit 15 interprets the posture to be taken by the subject 1 corresponding to the ascending colon, and determines that the posture to be taken by the subject 1, who includes the capsule endoscope 3 in the ascending colon, is the Trendelenburg's position. The control unit 15 controls the position display unit 12b to display a position image Q1 indicating that the capsule endoscope 3 has reached the ascending colon and the examination-procedure display unit 12c to display a posture image R1 indicating that the posture to be taken by the subject 1 is the Trendelenburg's position. Further, the control unit 15 controls the image display unit 12a to sequentially display the in-vivo images $P_n$ captured by the capsule endoscope 3 in the ascending colon (that is, an image of inside of ascending colon) on a real-time basis.

A user such as a doctor or nurse can observe the inside of the ascending colon of the subject 1 on a real-time basis by visually checking the in-vivo images $P_n$ of the inside of the ascending colon sequentially displayed on the image display unit 12a. Further, the user can understand that the capsule endoscope 3 inside the subject 1 has reached the ascending colon by visually checking the position image Q1 displayed on the position display unit 12b. Furthermore, the user can understand that the posture to be taken by the subject 1 is the Trendelenburg's position by visually checking the posture image R1 displayed on the examination-procedure display unit 12c. In this case, the user has the subject 1 changed the posture thereof on the bed 2 (supine posture) to the Trendelenburg's position according to an instruction given by the posture image R1.

When the posture of the subject 1 is changed to the Trendelenburg's position according to the instruction by the posture image R1, the capsule endoscope 3 inside the ascending colon of the subject 1 can smoothly advance in the ascending colon due to gravity or the like, and finally reaches the transverse colon. When the capsule endoscope 3 has reached the transverse colon, the control unit 15 understands that the intra-organ reached position of the capsule endoscope 3 is in the transverse colon based on the received field strength information acquired together with the in-vivo images $P_n$ captured by the capsule endoscope 3 in the transverse colon. In this case, the control unit 15 interprets the posture to be taken by the subject 1 corresponding to the transverse colon, and determines that the posture to be taken by the subject 1, who includes the capsule endoscope 3 in the transverse colon, is the left lateral decubitus position.

The control unit 15 controls the position display unit 12b to display a position image Q2 indicating that the capsule endoscope 3 has reached the transverse colon, instead of the position image Q1, and the examination-procedure display unit 12c to display a posture image R2 indicating that the posture to be taken by the subject 1 is the left lateral decubitus position. Further, the control unit 15 controls the image display unit 12a to sequentially display the in-vivo images $P_n$ captured by the capsule endoscope 3 in the transverse colon (that is, an image of inside of transverse colon) on a real-time basis.

A user such as a doctor or nurse can observe the inside of the transverse colon of the subject 1 on a real-time basis by visually checking the in-vivo images $P_n$ of the inside of the transverse colon sequentially displayed on the image display unit 12a. Further, the user can understand that the capsule endoscope 3 inside the subject 1 has reached the transverse colon by visually checking the position image Q2 displayed on the position display unit 12b. Furthermore, the user can understand that the posture to be taken by the subject 1 is the left lateral decubitus position by visually checking the posture image R2 displayed on the examination-procedure display unit 12c. In this case, the user has the subject 1 changed the posture thereof on the bed 2 (Trendelenburg's position) to the left lateral decubitus position according to an instruction given by the posture image R2.

When the posture of the subject 1 is changed to the left lateral decubitus position according to the instruction by the posture image R2, the capsule endoscope 3 inside the transverse colon of the subject 1 can smoothly advance in the transverse colon due to gravity or the like, and finally reaches the descending colon. When the capsule endoscope 3 has reached the descending colon, the control unit 15 ascertains that the intra-organ reached position of the capsule endoscope 3 is in the descending colon based on the received field strength information acquired together with the in-vivo images $P_n$ captured by the capsule endoscope 3 in the transverse colon. In this case, the control unit 15 interprets the posture to be taken by the subject 1 corresponding to the descending colon, and determines that the posture to be taken by the subject 1, who includes the capsule endoscope 3 in the descending colon, is the sitting position.

The control unit 15 controls the position display unit 12b to display a position image Q3 indicating that the capsule endoscope 3 has reached the descending colon, instead of the position image Q2, and the examination-procedure display unit 12c to display a posture image R3 indicating that the posture to be taken by the subject 1 is the sitting position. Further, the control unit 15 controls the image display unit 12a to sequentially display the in-vivo images $P_n$ captured by the capsule endoscope 3 in the descending colon (that is, an image of inside of descending colon) on a real-time basis.

A user such as a doctor or nurse can observe the inside of the descending colon of the subject 1 on a real-time basis by visually checking the in-vivo images $P_n$ of the inside of the descending colon sequentially displayed on the image display unit 12a. Further, the user can understand that the capsule endoscope 3 inside the subject 1 has reached the descending colon by visually checking the position image Q3 displayed on the position display unit 12b. Furthermore, the user can understand that the posture to be taken by the subject 1 is the sitting position by visually checking the posture image R3 displayed on the examination-procedure display unit 12c. In this case, the user has the subject 1 changed the posture thereof on the bed 2 (left lateral decubitus position) to the sitting position according to an instruction given by the posture image R3.

When the posture of the subject 1 is changed to the sitting position according to the instruction by the posture image R3, the capsule endoscope 3 inside the descending colon of the subject 1 can smoothly advance in the descending colon due to gravity or the like, and leaves the descending colon and finally reaches a sigmoidal colon. Thereafter, the capsule endoscope 3 smoothly advances sequentially in large intestine such as a sigmoidal colon and rectum with peristaltic movements, and finally, it is naturally excreted to outside of the subject 1.

When the subject 1 on the bed 2 maintains the supine posture, the capsule endoscope 3 in the subject 1 may stagnate inside large intestine internally washed for observation (for example, in ascending colon) for a long time. In this case, power shortfall of the battery held inside the casing of the capsule endoscope 3 occurs. As a result, the capsule endoscope 3 cannot sufficiently capture the in-vivo images of the entire region of from the ascending colon to the rectum of the large intestine, which is the observed region.

On the other hand, the display device 6 having the configuration described above displays the posture images R1 to R3 corresponding to the intra-organ reached position of the capsule endoscope 3, sequentially along a moving direction of the capsule endoscope 3 in the large intestine. When the posture of the subject 1 is sequentially changed according to the instruction by the posture images R1 to R3, the capsule endoscope 3 in the subject 1 can smoothly advance sequentially in the entire region of large intestine, that is, ascending colon, transverse colon, descending colon, and regions thereafter (such as sigmoidal colon or rectum).

The display device 6 that sequentially changes over and displays the posture images R1 to R3 can show a user or the subject 1 the posture to be taken by the subject 1 and a sequence of posture change so that the capsule endoscope 3 in the large intestine can smoothly advance sequentially, thereby enabling to support smooth movement of the capsule endoscope 3 in the large intestine. As a result of support by the display device 6, the capsule endoscope 3 in the subject 1 can sufficiently capture in-vivo image groups of the entire region of the large intestine to be observed, from the ascending colon to rectum. The display device 6 can sequentially display the in-vivo image groups of the inside of the large intestine captured by the capsule endoscope 3 on the image display unit 12a on a real-time basis.

As described above, according to the first embodiment of the present invention, the received field strength information, which is an example of information relating the position of the capsule endoscope inserted into the subject, is acquired together with the in-vivo images, and a capsule position in the subject is calculated based on the received field strength information. When the intra-organ reached position corresponding to the capsule position is at a position inside internal organs to be observed, the posture to be taken by the subject corresponding to the intra-organ reached position is determined, and the posture image indicating the determined posture is displayed. Therefore, the posture of the subject that accelerates the advancement of the capsule endoscope inside the subject can be sequentially displayed corresponding to the intra-organ reached position of the capsule endoscope. As a result, the posture to be taken by the subject and the sequence of posture change for accelerating the advancement of the capsule endoscope inserted into the subject can be indicated, and a display device that can support smooth advancement of the capsule endoscope having reached the inside of a desired internal organ such as large intestine, and an in-vivo information acquiring system using the same can be achieved.

Second Embodiment

A second embodiment of the present invention will be described next. In the first embodiment, when the intra-organ reached position is a predetermined reached position such as the observed region, the posture image indicating the posture to be taken by the subject 1 has been displayed. However, in the second embodiment, it is determined whether the capsule endoscope 3 in internal organs is in a stagnant state, and when the stagnant state continues for a predetermined time or longer and the intra-organ reached position is the predetermined reached position such as the observed region, a posture image indicating a posture to be taken by the subject 1 is displayed.

Figure 5:
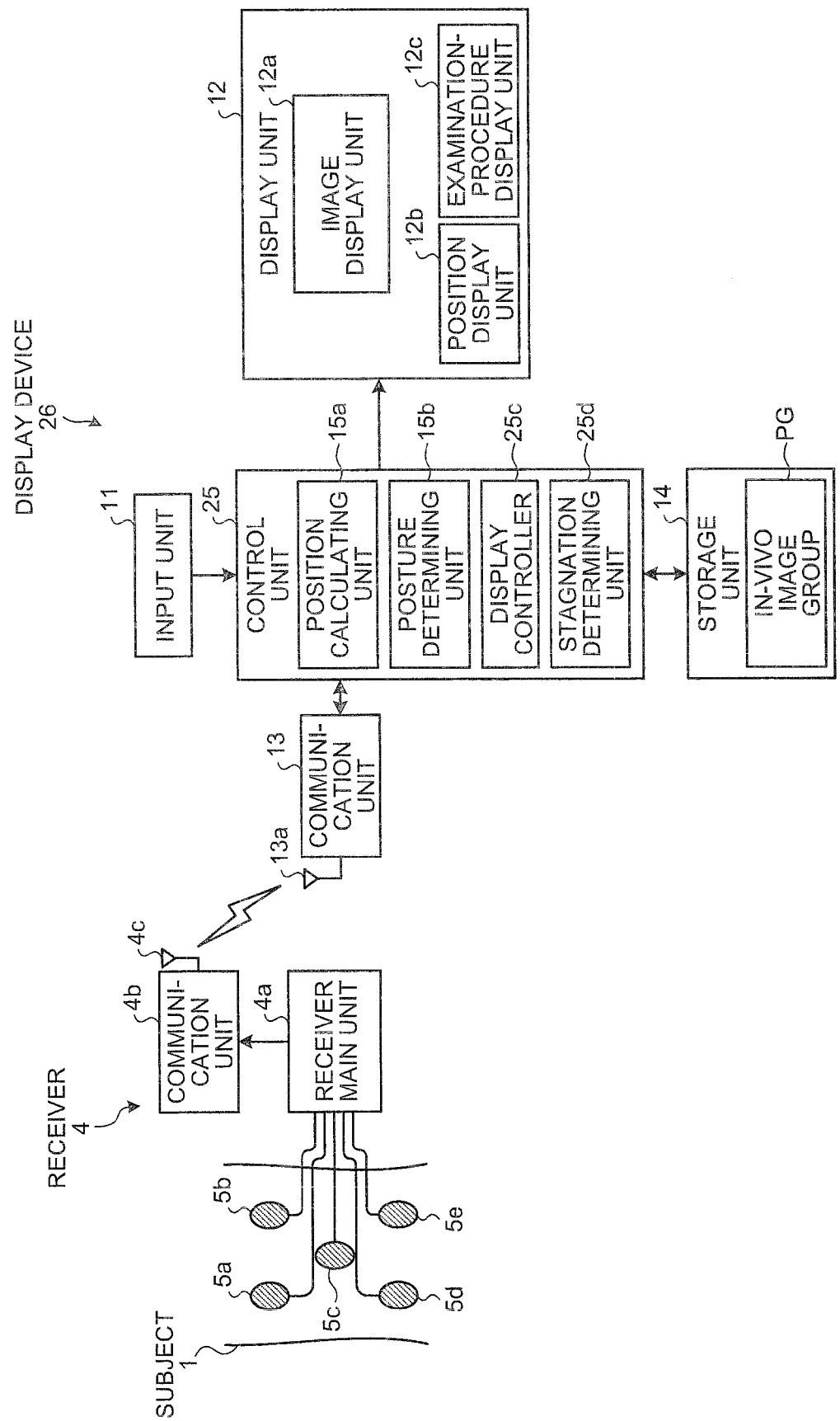
FIG. 5 is a block diagram for schematically depicting a configuration example of a display device according to a second embodiment of the present invention.

FIG. 5 is a block diagram for schematically depicting a configuration example of a display device according to the second embodiment of the present invention. In FIG. 5, a display device 26 according to the second embodiment includes a control unit 25 instead of the control unit 15 in the display device 6 according to the first embodiment. An in-vivo information acquiring system according to the second embodiment includes the display device 26 instead of the display device 6 in the in-vivo information acquiring system (see FIG. 1) according to the first embodiment. Other configurations of the second embodiment are the same as those of the first embodiment, and like component parts are denoted by like reference numerals or letters.

The control unit 25 determines whether the capsule endoscope 3 inserted into the subject 1 is in the stagnant state (hereinafter, also referred to as "stagnant state of the capsule"), and when the stagnant state of the capsule continues for a predetermined time or longer, functions to display a check window for checking whether the posture of the subject 1 is changed on the display unit 12. When a posture change instruction selected in the check window is input from the input unit 11 and the intra-organ reached position of the capsule endoscope 3 is at a predetermined reached position (for example, a position in large intestine, which is an observed region), the control unit 25 determines the posture to be taken by the subject 1 corresponding to the intra-organ reached position and functions to display the posture image indicating the determined posture of the subject 1 on the examination-procedure display unit 12c. Other functions of the control unit 25 are the same as those of the control unit 15 in the display device 6 according to the first embodiment.

The control unit 25 includes the position calculating unit 15a and the posture determining unit 15b like in the control unit 15 described above, and a display controller 25c instead of the display controller 15c in the control unit 15. The control unit 25 includes a stagnation determining unit 25d that determines the stagnant state of the capsule in the subject 1.

When the stagnant state of the capsule in the subject 1 continues for a predetermined time or longer, the display controller 25c performs control to display the check window for checking whether the posture of the subject 1 is to be changed on the display unit 12. The display controller 25c indicates that the capsule endoscope 3 in the subject 1 is in the stagnant state by displaying the check window on the display unit 12 and requests an input of an instruction whether to change the posture of the subject 1. Other functions of the display controller 25c are the same as those of the display controller 15c in the display device 6 according to the first embodiment.

The stagnation determining unit 25d determines whether the capsule endoscope 3 in the subject 1 is in the stagnant state (a stagnant state of the capsule). Specifically, the stagnation determining unit 25d determines whether the capsule endoscope 3 in the subject 1 is in the stagnant state of the capsule based on the capsule position calculated by the position calculating unit 15a. In this case, when an amount of change (displacement of the capsule endoscope 3) of the capsule position is within a predetermined range, the stagnation determining unit 25d determines that the capsule endoscope 3 is in the stagnant state of the capsule. The stagnation determining unit 25d also determines whether the stagnant state of the capsule continues for a predetermined time or longer (for example, longer than 5 seconds) based on acquisition time information of the in-vivo image of the subject 1 or imaging time information or the like of the in-vivo image sequentially acquired via the communication unit 13.

Figure 6:
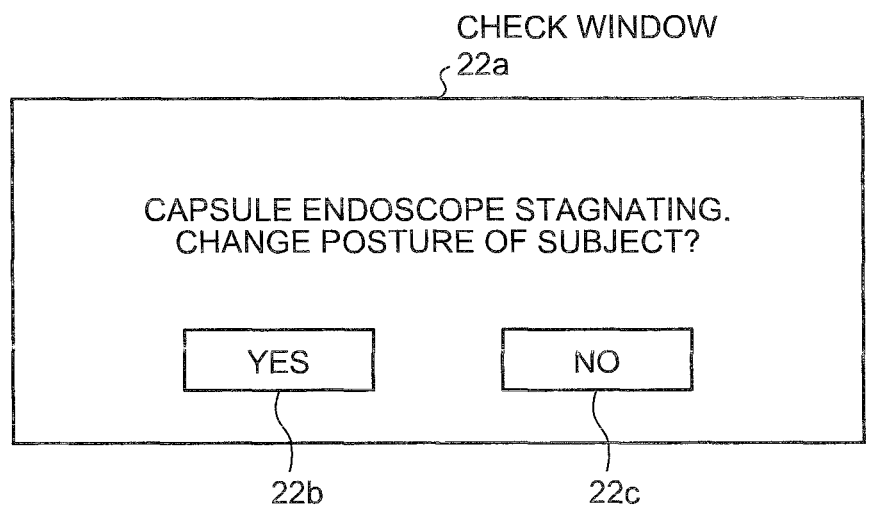
FIG. 6 is a schematic diagram of a specific example of a check window for checking whether a posture of a subject is to be changed.

The check window displayed on the display unit 12 by the display controller 25c will be specifically described next. FIG. 6 is a schematic diagram of a specific example of the check window for checking whether the posture of the subject 1 is to be changed. As shown in FIG. 6, a check window 22a indicates that the capsule endoscope 3 in the subject 1 is in the stagnant state, and includes selection buttons 22b and 22c for selecting and inputting an instruction whether to change the posture of the subject 1. The check window 22a is a request screen for requesting an input of the instruction whether to change the posture of the subject 1 when the stagnant state of the capsule continues in the subject 1 for a predetermined time or longer.

When the stagnant state of the capsule continues in the subject 1 for a predetermined time or longer, the display controller 25c performs control to display the check window 22a on the display unit 12. Accordingly, the control unit 25 confirms whether to change the posture of the subject 1. Specifically, when any one of selection buttons 22b and 22c in the check window 22a is clicked, the control unit 25 confirms the instruction whether to change the posture of the subject 1 based on the instruction information input from the input unit 11.

Figure 7:
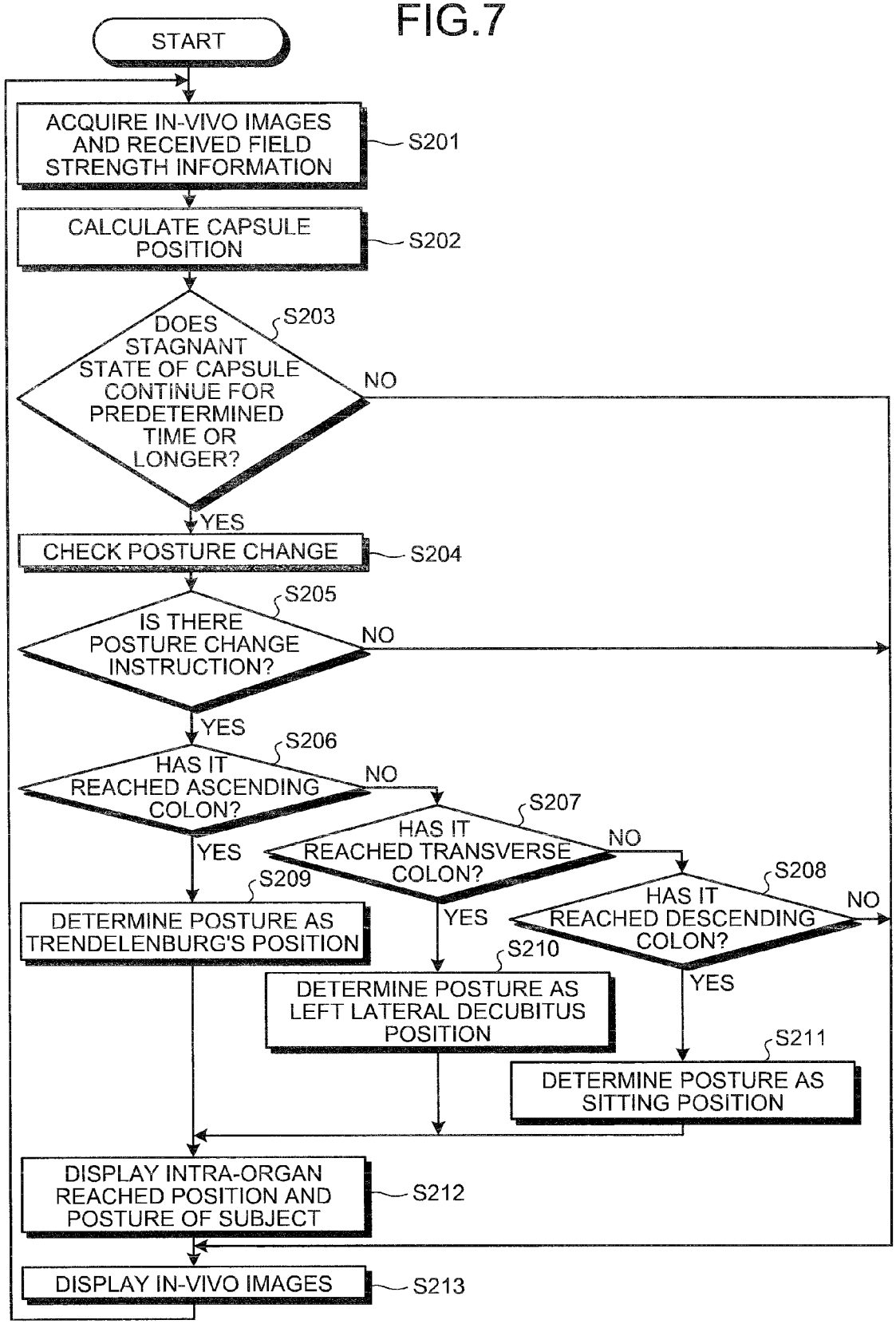
FIG. 7 is a flowchart for exemplifying a process procedure performed by a control unit of a display device according to the second embodiment of the present invention.

An operation of the control unit 25 in the display device 26 according to the second embodiment of the present invention will be described next. FIG. 7 is a flowchart of a process procedure performed by the control unit 25 in the display device 26 according to the second embodiment of the present invention. The control unit 25 determines whether the capsule endoscope 3 in the subject 1 is in the stagnant state based on the capsule position calculated every time the in-vivo image of the subject 1 is acquired via the communication unit 13, and confirms whether to change the posture of the subject 1 when the stagnant state of the capsule in the subject 1 continues for a predetermined time or longer. When having confirmed the instruction to change the posture of the subject 1, the control unit 25 determines the posture to be taken by the subject 1 corresponding to the intra-organ reached position of the capsule endoscope 3 in the subject 1, and controls the examination-procedure display unit 12c to display the posture image indicating the determined posture. Other process procedures executed by the control unit 25 are substantially the same as the process procedures (see FIG. 3) of the control unit 15 in the display device 6 according to the first embodiment.

That is, as shown in FIG. 7, the control unit 25 acquires the in-vivo image of the subject 1 and the received field strength information via the communication unit 13 similarly to the above-described Steps S101 and S102 (Step S201), and calculates the capsule position based on the received field strength information acquired together with the in-vivo image (Step S202).

The control unit 25 then determines whether the stagnant state of the capsule continues for a predetermined time or longer in the subject 1 (Step S203). Specifically, the stagnation determining unit 25d calculates an amount of change of the capsule position calculated by the position calculating unit 15a at Step S202, and when the calculated amount of change of the capsule position is within a predetermined range, determines that the capsule endoscope in the subject 1 is stagnating (that is, in a stagnant state of the capsule). The stagnation determining unit 25d calculates an elapsed time after the capsule endoscope 3 in the subject 1 stagnates, based on the imaging time information or acquisition time information of the in-vivo images acquired at Step S201, and when a calculated elapsed time is longer than a predetermined time (for example, longer than 5 seconds), determines that the stagnant state of the capsule continues for a predetermined time or longer.

When having determined that the stagnant state of the capsule continues for a predetermined time or longer (Yes at Step S203), the control unit 25 confirms whether to change the posture of the subject 1 who has the stagnating capsule endoscope 3 in his internal organ (Step S204), and determines whether there is a posture change instruction of the subject 1 based on the check result of the posture change instruction (Step S205). In this case, the display controller 25c performs control to display the check window 22a on the display unit 12, using the fact that the stagnant state of the capsule continues for a predetermined time or longer as a trigger. Accordingly, the display controller 25c requests an input of an instruction indicating whether to change the posture of the subject 1. The control unit 25 confirms the instruction indicating whether to change the posture of the subject 1 based on instruction information input from the input unit 11 by clicking any one of the selection buttons 22b and 22c included in the check window 22a.

Specifically, when the selection button 22b in the check window 22a is selected by an clicking operation using the input unit 11, the control unit 25 confirms the instruction for changing the posture of the subject 1 based on posture change instruction information input by the input unit 11 in response to the clicking operation of the selection button 22b. In this case, the control unit 25 determines that there is the posture change instruction of the subject 1 (Yes at Step S205), and determines whether the capsule endoscope 3 in the subject 1 has reached a predetermined intra-organ reached position (that is, a position in large intestine, which is the internal organ to be observed) similarly to the above-described Steps S103 to S105.

That is, when there is the posture change instruction of the subject 1, the control unit 25 determines whether the capsule endoscope 3 has reached the ascending colon similarly to Step S103 (Step S206). When having determined that the capsule endoscope 3 has not reached the ascending colon (No at Step S206), the control unit 25 determines whether the capsule endoscope 3 has reached the transverse colon (Step S207). When having determined that the capsule endoscope 3 has not reached the transverse colon (No at Step S207), the control unit 25 determines whether the capsule endoscope 3 has reached the descending colon similarly to Step S105 (Step S208).

On the other hand, when having determined that the capsule endoscope 3 has reached the ascending colon at Step S206 (Yes at Step S206), the control unit 25 sets the posture to be taken by the subject 1 as the Trendelenburg's position similarly to the above-described Step S106 (Step S209). When having determined that the capsule endoscope 3 has reached the transverse colon at Step S207 (Yes at Step S207), the control unit 25 sets the posture to be taken by the subject 1 as the left lateral decubitus position similarly to the above-described Step S107 (Step S210). When having determined that the capsule endoscope 3 has reached the descending colon at Step S208 (Yes at Step S208), the control unit 25 sets the posture to be taken by the subject 1 as the sitting position as the above-described Step S108 (Step S211).

The control unit 25 controls the display unit 12 to display the intra-organ reached position of the capsule endoscope 3 in the subject 1 and the posture of the subject 1 similarly to the above-described Step S109 after setting the posture to be taken by the subject 1 by performing any one of process procedures at Steps S209 to S211 (Step S212). In this case, the display controller 25c performs control to display a position image and a posture image corresponding to the intra-organ reached position of the capsule endoscope 3 on the position display unit 12b and the examination-procedure display unit 12c, respectively, like the display controller 15c of the display device 6 in the first embodiment.

The control unit 25 controls the display unit 12 to display the in-vivo images of the subject 1 acquired at Step S201 similarly to the above-described Step S110 (Step S213). In this case, the display controller 25c performs control to display the in-vivo images of the subject 1 acquired at Step S201 (that is, in-vivo images stored in the storage unit 14 at Step S201) on the image display unit 12a, like the display controller 15c of the display device 6 in the first embodiment. Thereafter, the control unit 25 returns to Step S201 to repeat the process procedures at Step S201 and onwards.

On the other hand, at Step S205, when the selection button 22c is selected by the clicking operation using the input unit 11, the control unit 25 confirms the instruction indicating that the posture of the subject 1 is not changed, based on the instruction information indicating that the posture of the subject 1 is not changed input by the input unit 11 in response to the clicking operation of the selection button 22c. In this case, the control unit 25 determines that there is no posture change instruction of the subject 1 (No at Step S205), and proceeds to Step S213 to repeat the process procedures at Step S213 and onwards.

When having determined that the stagnant state of the capsule does not continue for a predetermined time or longer at Step S203 (No at Step S203), or when having determined that the capsule endoscope 3 has not yet reached the descending colon at Step S208 (No at Step S208), the control unit 25 proceeds to Step S213 to repeat the process procedures at Step S213 and onwards.

Figure 8:
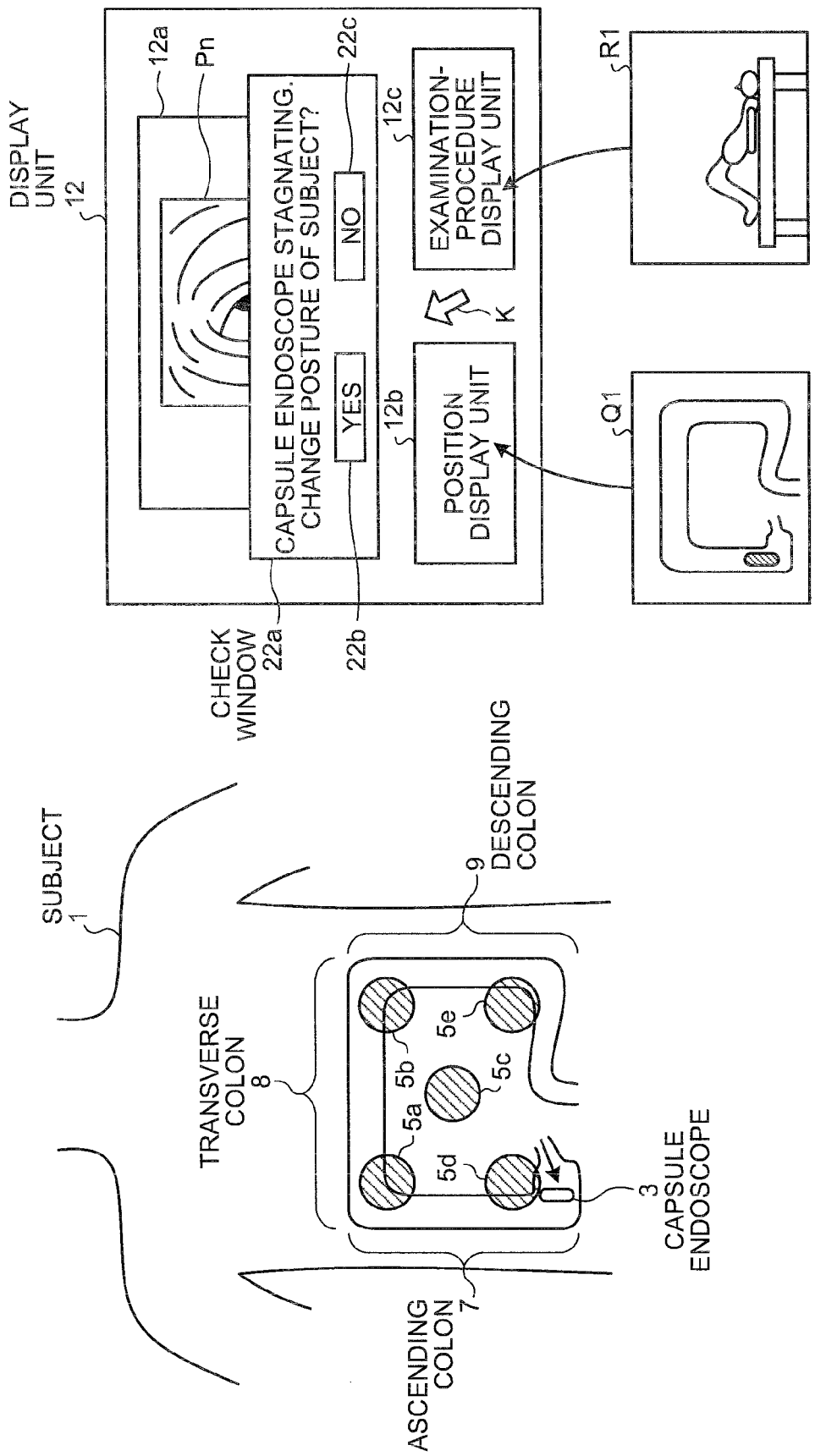
FIG. 8 is a schematic diagram for specifically explaining an operation of the control unit of the display device according to the second embodiment of the present invention.

An operation of the control unit 25 in the display device 26 according to the second embodiment of the present invention will be specifically described next by exemplifying a case that large intestine of the subject 1 is an observed region. FIG. 8 is a schematic diagram for specifically explaining the operation of the control unit 25 in the display device 26 according to the second embodiment of the present invention. The operation of the control unit 25 will be specifically described below with reference to FIG. 8.

Similarly to the first embodiment described above, the capsule endoscope 3 is swallowed from the mouth of the subject 1, and sequentially passes through the esophagus, stomach, and small intestine with peristaltic movements. While the capsule endoscope 3 sequentially advances inside the internal organs of the subject 1, the control unit 25 calculates a capsule position at the time of capturing the in-vivo image $P_n$, every time the in-vivo image $P_n$ captured by the capsule endoscope 3 is acquired, like the control unit 15 in the display device 6 according to the first embodiment.

The capsule endoscope 3 in the subject 1 sequentially passes through the esophagus, stomach, and small intestine with peristaltic movements without stagnating in the internal organ for a predetermined time or longer (for example, longer than 5 seconds) until reaching the large intestine. In this case, the control unit 25 ascertains that the stagnant state of the capsule in the subject 1 does not continue for a predetermined time or longer based on the capsule position calculated every time the in-vivo image $P_n$ is acquired. The control unit 25 controls the image display unit 12a to sequentially display the in-vivo images $P_n$ sequentially acquired via the communication unit 13.

The capsule endoscope 3 leaves the small intestine in the subject 1, who is taking the supine posture on the bed 2, and reaches an ascending colon 7. The large intestine to be observed of the subject 1 has been internally washed beforehand. Accordingly, it is difficult for the capsule endoscope 3 to smoothly advance in the ascending colon 7 only with peristaltic movements, and stagnates in the ascending colon 7 (for example, near entrance from small intestine). The capsule endoscope 3 sequentially captures the in-vivo images of the ascending colon and sequentially wirelessly transmits the captured in-vivo images to outside, while stagnating in the ascending colon 7.

The received field strength of the receiving antennas 5a to 5e that capture image signals wirelessly transmitted from the stagnating capsule endoscope 3 is strongest at the receiving antenna 5d arranged closest to the stagnating capsule endoscope 3, and becomes weaker with an increase of the distance from the stagnating capsule endoscope 3 to the other receiving antennas 5a, 5b, 5c, and 5e. The received field strength of the receiving antennas 5a to 5e is substantially constant for each of the receiving antennas 5a to 5e and the amount of change of the received field strength is within a predetermined range, so long as the stagnant state of the capsule continues.

The control unit 25 sequentially acquires the received field strength information including the respective received field strengths of the receiving antennas 5a to 5e together with the in-vivo images $P_n$, and sequentially calculates the capsule position based on the received field strength information. Because the amount of change in the respective received field strength of each receiving antenna 5a to 5e included in the received field strength information is within the predetermined range, the amount of change of the respective capsule positions sequentially calculated by the control unit 25 is within the predetermined range. In this case, the control unit 25 ascertains that the capsule position calculated based on the received field strength information corresponds to an end of the ascending colon 7 (vicinity of entrance from small intestine), and determines that the capsule endoscope 3 in the ascending colon 7 is stagnating based on a fact that the amount of change of the capsule position is within the predetermined range.

Further, the control unit 25 determines that the stagnant state of the capsule in the ascending colon 7 continues for a predetermined time or longer (for example, longer than 5 seconds) based on the imaging time information or the acquisition time information of the in-vivo images $P_n$ sequentially acquired together with the received field strength information. In this case, the control unit 25, as shown in FIG. 8, performs control to display the in-vivo images $P_n$ on the image display unit 12a and performs control to display the check window 22a on the display unit 12.

When the check window 22a is displayed on the display unit 12, a user such as a doctor or nurse can recognize that the capsule endoscope 3 in the subject 1 has reached the large intestine by visually checking the in-vivo images $P_n$ displayed on the image display unit 12a. In this case, the user adjusts a cursor K to the selection button 22b by using the input unit 11 and clicks the selection button 22b. The input unit 11 inputs the instruction information corresponding to the selection button 22b, that is, the instruction information instructing the subject 1 to change the posture, to the control unit 25.

The control unit 25 determines that there is the posture change instruction of the subject 1 based on posture change instruction information input from the input unit 11, and sets the Trendelenburg's position corresponding to the ascending colon 7, which is the intra-organ reached position of the stagnating capsule endoscope 3, as the posture to be taken by the subject 1. In this case, the control unit 25 performs control to display a position image Q1 indicating that the intra-organ reached position is the ascending colon 7 (near entrance from small intestine) on the position display unit 12b and performs control to display the posture image R1 indicating that the posture to be taken by the subject 1 is the Trendelenburg's position on the examination-procedure display unit 12c.

The control unit 25 performs control to display the in-vivo images $P_n$ sequentially acquired via the communication unit 13 on the image display unit 12a on a real-time basis, and calculates the capsule position every time the in-vivo image $P_n$ is acquired, to determine whether the stagnant state of the capsule continues for a predetermined time or longer based on the capsule position. When having determined that the stagnant state of the capsule continues for a predetermined time or longer, the control unit 25 performs control to display the check window 22a on the display unit 12 in each case. That is, the check window 22a is displayed on the display unit 12 every time the capsule endoscope 3 continuously stagnates in a transverse colon 8 or a descending colon 9 of the subject 1 for a predetermined time or longer.

When the posture change instruction information corresponding to the selection button 22b in the check window 22a is input, the control unit 25 determines the posture to be taken by the subject 1 corresponding to the intra-organ reached position of the capsule endoscope 3 in each case. Specifically, when the intra-organ reached position of the stagnating capsule endoscope 3 changes from the ascending colon 7 to the transverse colon 8, the control unit 25 performs control to display a position image Q2 corresponding to the transverse colon 8 instead of the position image Q1 on the position display unit 12b, and performs control to display a posture image R2 corresponding to the transverse colon 8 instead of the posture image R1 on the examination-procedure display unit 12c. When the intra-organ reached position of the stagnating capsule endoscope 3 changes from the transverse colon 8 to the descending colon 9, the control unit 25 performs control to display a position image Q3 corresponding to the descending colon 9 instead of the position image Q2 on the position display unit 12b, and performs control to display a posture image R3 corresponding to the descending colon 9 instead of the posture image R2 on the examination-procedure display unit 12c.

When the instruction information indicating that the posture is not to be changed is input corresponding to the selection button 22c of the check window 22a, the control unit 25 displays the in-vivo images $P_n$ on the image display unit 12a without changing the position image currently displayed on the position display unit 12b, the posture image currently displayed on the examination-procedure display unit 12c, or the state where image is not displayed on the position display unit 12b and the examination-procedure display unit 12c.

As described above, according to the second embodiment, the capsule position in the subject is calculated to determine whether the capsule endoscope in the subject is stagnating based on the amount of change of the capsule position, and when the determined stagnant state of the capsule continues for a predetermined time or longer, the posture to be taken by the subject corresponding to the intra-organ reached position of the stagnating capsule endoscope is determined to display the posture image indicating the determined posture similarly to the first embodiment. Accordingly, the display device that can indicate the posture of the subject, which accelerates the advancement of the stagnating capsule endoscope when the capsule endoscope is stagnating in an internal organ, can secure the same operations and effects as those in the first embodiment, and can reduce the burden on the subject, who changes the posture corresponding to the intra-organ reached position of the capsule endoscope, and the in-vivo information acquiring system using the display device can be achieved.

When the stagnant state of the capsule continues for a predetermined time or longer, a request screen for requesting an input of an instruction whether to change the posture of the subject is displayed, and when a posture change instruction selected from the request screen is input, the posture to be taken by the subject is determined based on the posture change instruction and a posture image indicating the determined posture is displayed. Accordingly, it can be easily confirmed whether the stagnant position of the capsule endoscope stagnating in the subject is at a position in a desired internal organ such as large intestine, and the posture to be taken by the subject can be displayed when the capsule endoscope reaches the desired internal organ.

Modified Example of the Second Embodiment

A modified example of the second embodiment of the present invention will be described next. In the second embodiment, the capsule position is calculated based on the received field strength information associated with an in-vivo image every time the in-vivo image of the subject 1 is acquired. However, in the modified example of the second embodiment, it is determined whether the capsule endoscope 3 in an internal organ is in a stagnant state, and when the capsule endoscope is in the stagnant state of the capsule, the capsule position is calculated.

Figure 9:
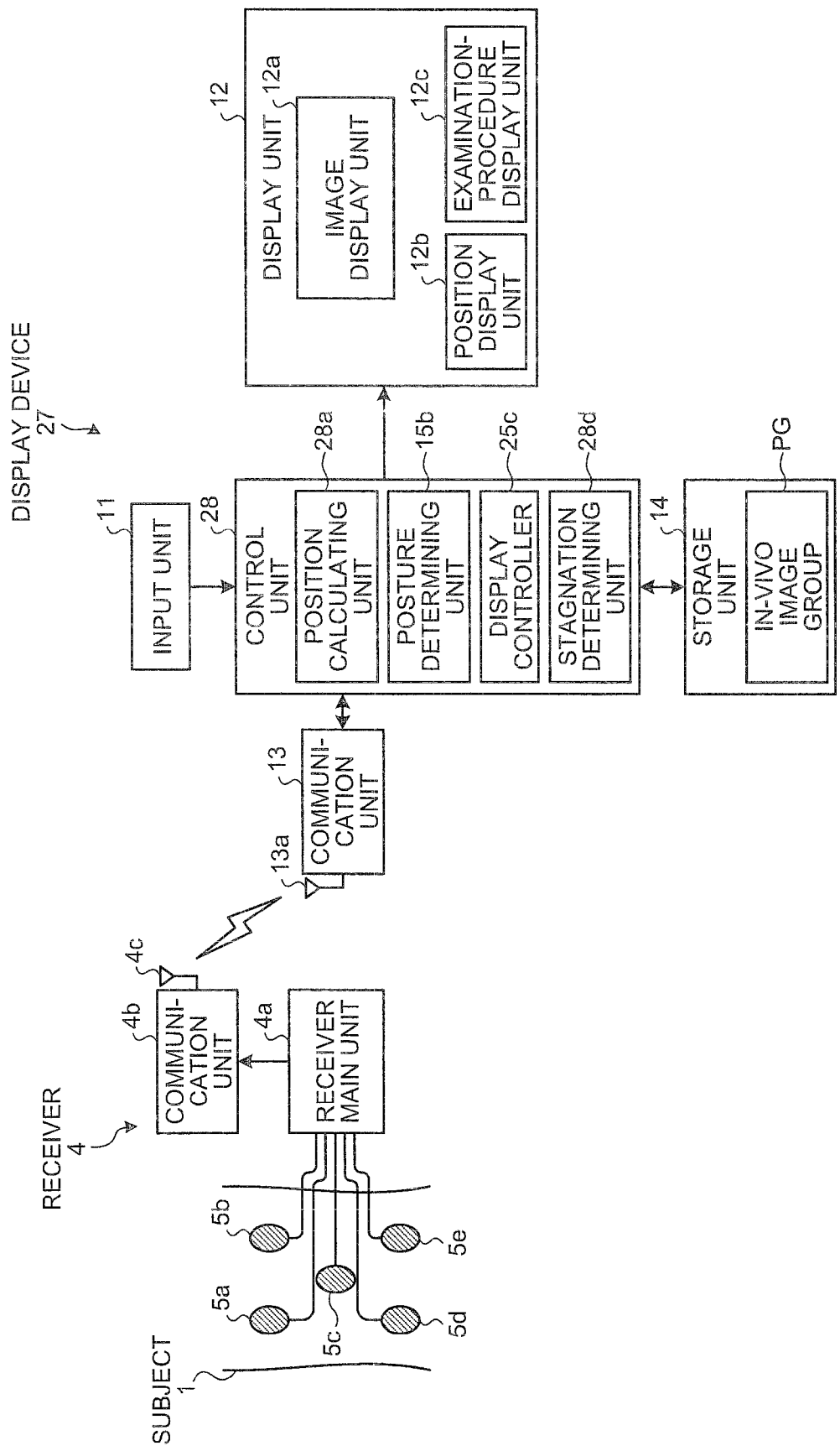
FIG. 9 is a block diagram for schematically depicting a configuration example of a display device according to a modified example of the second embodiment of the present invention.

FIG. 9 is a block diagram for schematically depicting a configuration example of the display device according to the modified example of the second embodiment of the present invention. As shown in FIG. 9, a display device 27 according to the modified example of the second embodiment includes a control unit 28 instead of the control unit 25 in the display device 26 according to the second embodiment. The in-vivo information acquiring system according to the modified example of the second embodiment of the present invention includes the display device 27 instead of the display device 26 in the in-vivo information acquiring system according to the second embodiment. Other configurations of the modified example are the same as those of the second embodiment, and like component parts are denoted by like reference numerals or letters.

The control unit 28 determines whether the stagnant state of the capsule in the subject 1 continues for a predetermined time or longer based on the received field strength information acquired together with the in-vivo images of the subject 1, and calculates the capsule position when the stagnant state of the capsule continues for a predetermined time or longer. When the intra-organ reached position of the capsule endoscope 3 corresponding to the calculated capsule position is a predetermined reached position (for example, a position inside large intestine to be observed), the control unit 28 determines the posture to be taken by the subject 1 corresponding to the intra-organ reached position and controls the examination-procedure display unit 12c to display a posture image indicating the determined posture of the subject 1. Other functions of the control unit 28 are the same as those of the control unit 25 in the display device 26 according to the second embodiment.

The control unit 28 includes the posture determining unit 15b and the display controller 25c like the above-described control unit 25. The control unit 28 also includes a position calculating unit 28a instead of the position calculating unit 15a of the control unit 25, and a stagnation determining unit 28d instead of the stagnation determining unit 25d.

When the stagnant state of the capsule continues for a predetermined time or longer in the subject 1, the position calculating unit 28a calculates the position of the stagnating capsule endoscope 3 (a capsule position in the stagnant state) based on the received field strength information associated with the in-vivo image of the subject 1. Specifically, when the stagnant state of the capsule continues for a predetermined time or longer and a posture change instruction of the subject 1 is input, the position calculating unit 28a calculates the capsule position in the stagnant state. Further, the position calculating unit 28a calculates the intra-organ reached position of the stagnating capsule endoscope 3 based on the capsule position in the stagnant state, and specifies the intra-organ reached position corresponding to the in-vivo image captured by the stagnating capsule endoscope 3 and the capsule position in the stagnant state. That is, the position calculating unit 28a is the same as the position calculating unit 15a in the display device 26 according to the second embodiment except that the calculation timing of the capsule position is different.

The stagnation determining unit 28d determines whether the capsule endoscope 3 in the subject 1 is in the stagnant state in the internal organ based on the received field strength information associated with the in-vivo image every time the in-vivo image of the subject 1 is acquired via the communication unit 13. In this case, the stagnation determining unit 28d calculates the amount of change in the received field strength of each receiving antenna included in the received field strength information, and when the amount of change in the received field strength of each receiving antenna is within a predetermined range, determines that the capsule endoscope is in the stagnant state of the capsule. When having determined that the capsule endoscope is in the stagnant state of the capsule, the stagnation determining unit 28d determines whether the stagnant state of the capsule continues for a predetermined time or longer (for example, longer than 5 seconds) based on the acquisition time information of the in-vivo image or the imaging time information of the in-vivo image of the subject 1 sequentially acquired via the communication unit 13.

Figure 10:
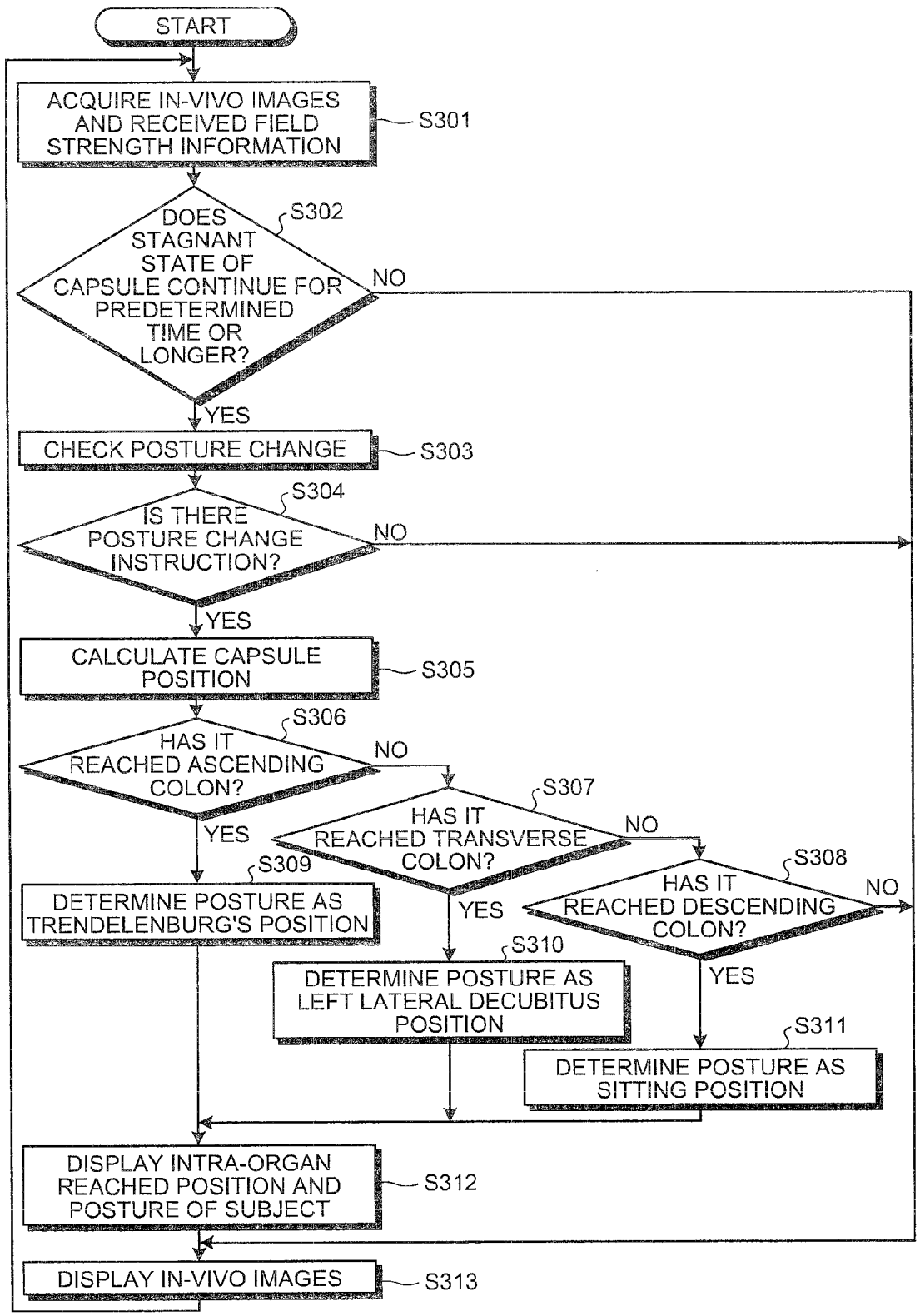
FIG. 10 is a flowchart for exemplifying a process procedure performed by a control unit of a display device according to the modified example of the second embodiment of the present invention.

An operation of the control unit 28 of the display device 27 according to the modified example of the second embodiment of the present invention will be described next. FIG. 10 is a flowchart of a process procedure performed by the control unit 28 of the display device 27 according to the modified example of the second embodiment of the present invention.

The control unit 28 determines whether the stagnant state of the capsule in the subject 1 continues for a predetermined time or longer based on the received field strength information acquired together with the in-vivo images of the subject 1. The control unit 28 calculates the capsule position when the stagnant state of the capsule continues for a predetermined time or longer and the posture change instruction of the subject 1 is input, and calculates the intra-organ reached position corresponding to the calculated capsule position. When the intra-organ reached position is a position inside large intestine (any one of ascending colon, transverse colon, or descending colon), the control unit 28 determines the posture to be taken by the subject 1 corresponding to the intra-organ reached position, and controls the examination-procedure display unit 12c to display the posture image indicating the determined posture.

That is, as shown in FIG. 10, the control unit 28 acquires the in-vivo images of the subject 1 and the received field strength information via the communication unit 13 similarly to the above-described Step S201 (Step S301). The control unit 28 then determines whether the stagnant state of the capsule continues for a predetermined time or longer in the subject 1 (Step S302).

Specifically, the stagnation determining unit 28d calculates the amount of change in the received field strength of each receiving antenna based on the received field strength information acquired together with the in-vivo images at Step S301, and when the calculated amount of change in the received field strength is within a predetermined range, determines that the capsule endoscope in the subject 1 is stagnating (that is, in a stagnant state of the capsule). The stagnation determining unit 28d calculates elapsed time after the capsule endoscope 3 in the subject 1 stagnates, based on the imaging time information or acquisition time information of the in-vivo images acquired at Step S201, and when the calculated elapsed time is longer than a predetermined time (for example, longer than 5 seconds), determines that the stagnant state of the capsule continues for a predetermined time or longer.

When having determined that the stagnant state of the capsule continues for a predetermined time or longer (Yes at Step S302), the control unit 28 confirms whether to change the posture of the subject 1 who has the stagnating capsule endoscope 3 in his internal organ similarly to the above-described Step S204 (Step S303). The control unit 28 then determines whether there is a posture change instruction of the subject 1 similarly to the above-described Step S205 (Step S304), and when having determined that there is the posture change instruction of the subject 1, calculates the stagnating capsule position (Step S305) (Yes at Step S304). In this case, the position calculating unit 28a calculates the stagnating capsule position based on the received field strength information acquired together with the in-vivo images at Step S301.

The control unit 28 determines whether the stagnating capsule endoscope 3 has reached the predetermined intra-organ reached position (that is, a position in large intestine, which is the internal organ to be observed). Specifically, the control unit 28 determines whether the stagnating capsule endoscope 3 has reached the ascending colon similarly to the above-described Step S206 (Step S306). When having determined that the stagnating capsule endoscope 3 has not reached the ascending colon (No at Step S306), the control unit 28 determines whether the stagnating capsule endoscope 3 has reached the transverse colon similarly to the above-described Step S207 (Step S307). When having determined that the stagnating capsule endoscope 3 has not reached the transverse colon (No at Step S307), the control unit 28 determines whether the stagnating capsule endoscope 3 has reached the descending colon similarly to the above-described Step S208 (Step S308).

On the other hand, when having determined that the stagnating capsule endoscope 3 has reached the ascending colon at Step S306 (Yes at Step S306), the control unit 28 sets the posture to be taken by the subject 1 as the Trendelenburg's position similarly to the above-described Step S209 (Step S309). When having determined that the stagnating capsule endoscope 3 has reached the transverse colon at Step S307 (Yes at Step S307), the control unit 28 sets the posture to be taken by the subject 1 as the left lateral decubitus position similarly to the above-described Step S210 (Step S310). When having determined that the stagnating capsule endoscope 3 has reached the descending colon at Step S308 (Yes at Step S308), the control unit 28 sets the posture to be taken by the subject 1 as the sitting position similarly to the above-described Step S211 (Step S311).

The control unit 28 controls the display unit 12 to display the intra-organ reached position of the capsule endoscope 3 in the subject 1 and the posture of the subject 1 similarly to the above-described Step S212 after setting the posture to be taken by the subject 1 by performing any one of process procedures at Steps S309 to S311 (Step S312). Subsequently, the control unit 28 controls the display unit 12 to display the in-vivo images of the subject 1 acquired at Step S301 similarly to the above-described Step S213 (Step S313). Thereafter, the control unit 28 returns to Step S301 to repeat the process procedures at Step S201 and onwards.

When having determined that the stagnant state of the capsule does not continue for a predetermined time or longer at Step S302 (No at Step S302), when having determined that there is no posture change instruction of the subject 1 at Step S304 (No at Step S304), or when having determined that the stagnating capsule endoscope 3 has not yet reached the descending colon at Step S308 (No at Step S308), the control unit 28 proceeds to Step S313 to repeat the process procedures at Step S313 and onwards.

As described above, in the modified example of the second embodiment of the present invention, the amount of change in the received field strength information associated with the in-vivo image is calculated every time the in-vivo image of the subject 1 is acquired, to determine whether the capsule endoscope in the subject is stagnating based on the calculated amount of change in the received field strength information. When the determined stagnant state of the capsule continues for a predetermined time or longer, the capsule position in the stagnant state is calculated, and the intra-organ reached position of the stagnating capsule endoscope is calculated based on the calculated capsule position in the stagnant state. The posture to be taken by the subject corresponding to the calculated reached position in the internal organ is determined to display the posture image indicating the determined posture. Accordingly, the display device that can efficiently calculate the position of the stagnating capsule endoscope in the subject, can secure the same operations and effects as those of the second embodiment, and can increase processing speed, and the in-vivo information acquiring system using the display device can be achieved.

Further, when the stagnant state of the capsule continues for a predetermined time or longer, the request screen for requesting an input of an instruction whether to change the posture of the subject is displayed, and when a posture change instruction selected from the request screen is input, the capsule position in the stagnant state is calculated based on the posture change instruction. When the calculated capsule position in the stagnant state corresponds to the predetermined intra-organ reached position, the posture to be taken by the subject corresponding to the intra-organ reached position is determined, and the posture image indicating the determined posture is displayed. Accordingly, similarly to the second embodiment described above, it can be easily confirmed whether the stagnant position of the capsule endoscope stagnating in the subject is at a position in a desired internal organ such as large intestine, and the posture to be taken by the subject can be displayed when the capsule endoscope reaches the desired internal organ.

Third Embodiment

A third embodiment of the present invention will be described next. In the second embodiment, the posture to be taken by the subject 1 is informed to the user or the like by displaying the posture image on the examination-procedure display unit 12c. However, in the third embodiment, the posture to be taken by the subject 1 is also informed by outputting speech information.

Figure 11:
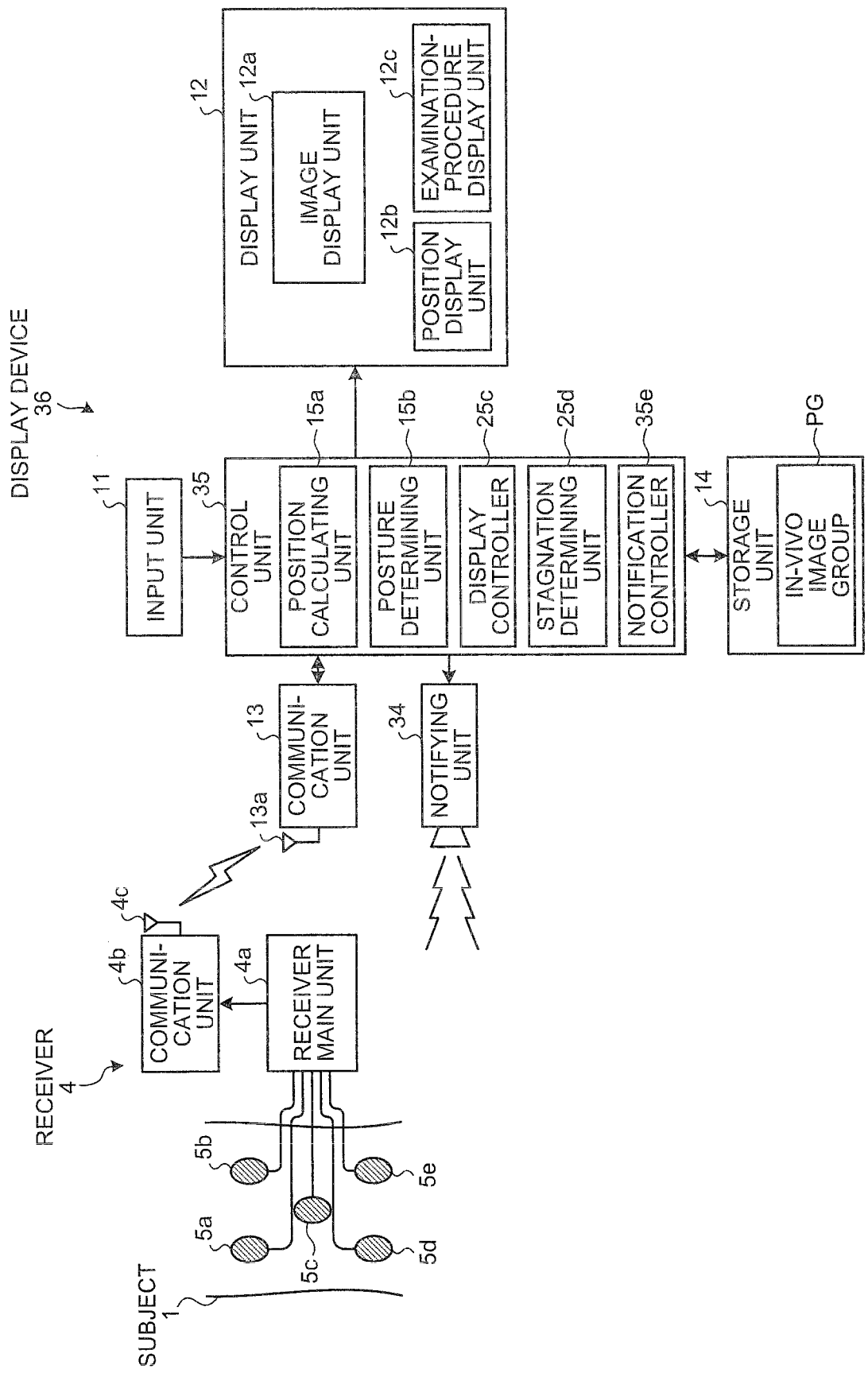
FIG. 11 is a block diagram schematically depicting a configuration example of a display device according to a third embodiment of the present invention.

FIG. 11 is a block diagram for schematically depicting a configuration example of a display device according to the third embodiment of the present invention. As shown in FIG. 11, a display device 36 according to the third embodiment includes a control unit 35 instead of the control unit 25 in the display device 26 according to the second embodiment, and also includes a notifying unit 34 that notifies of the speech information indicating the posture to be taken by the subject 1. The in-vivo information acquiring system according to the third embodiment of the present invention includes the display device 36 instead of the display device 26 in the in-vivo information acquiring system according to the second embodiment. Other configurations of the third embodiment are the same as those of the second embodiment, and like component parts are denoted by like reference numerals or letters.

The notifying unit 34 notifies of the speech information indicating the posture to be taken by the subject 1 who has the capsule endoscope 3 in his internal organ. Specifically, the notifying unit 34 outputs the speech information corresponding to the posture to be taken by the subject 1 indicated by the posture image displayed on the examination-procedure display unit 12c, thereby informing the subject 1 or a user such as a doctor or nurse of the posture to be taken by the subject 1. The speech information notified by the notifying unit 34 can indicate the posture itself to be taken by the subject 1 (for example, "Trendelenburg's position", "left lateral decubitus position", or "sitting position"), or can indicate a content for explaining the posture to be taken by the subject 1.

The control unit 35 controls the notifying unit 34 to notify of the speech information indicating the posture to be taken by the subject 1 corresponding to the intra-organ reached position of the capsule endoscope 3 in the subject 1. Other functions of the control unit 35 are the same as those of the control unit 25 in the display device 26 according to the second embodiment. The control unit 35 includes the position calculating unit 15a, the posture determining unit 15b, the display controller 25c, and the stagnation determining unit 25d, like the control unit 25, and also includes a notification controller 35e that controls the notifying unit 34.

The notification controller 35e controls the notifying unit 34 to notify of the speech information indicating the posture to be taken by the subject 1 who has the capsule endoscope 3 in his internal organ. Specifically, the notification controller 35e generates the speech information indicating the posture to be taken by the subject 1 determined by the posture determining unit 15b, and controls the notifying unit 34 to notify of generated speech information. The speech information notified by the notifying unit 34 instructed by the notification controller 35e corresponds to the posture of the subject 1 indicated by the posture image displayed on the examination-procedure display unit 12c.

Figure 12:
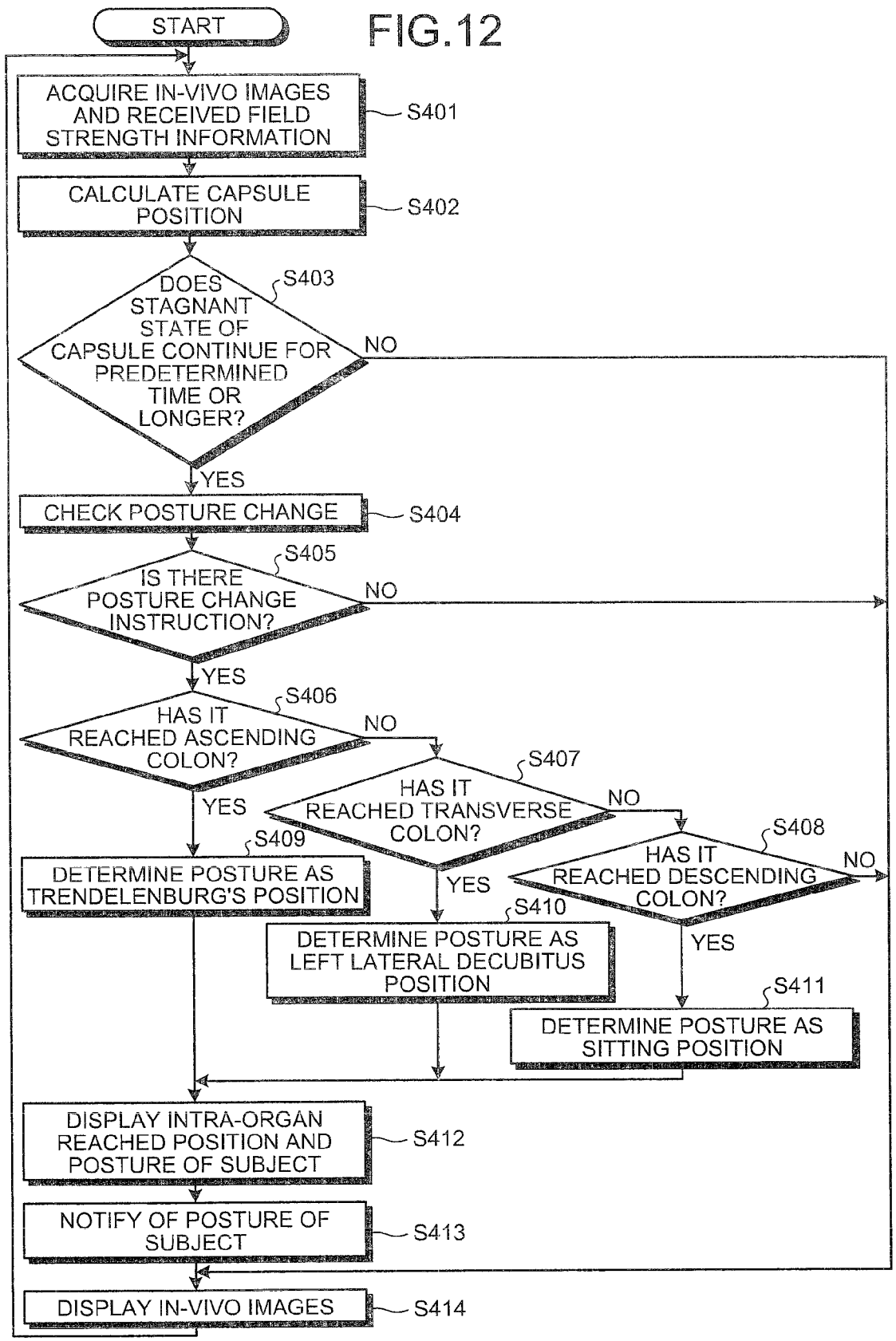
FIG. 12 is a flowchart of a process procedure performed by a control unit of the display device according to the third embodiment of the present invention.

An operation of the control unit 35 in the display device 36 according to the third embodiment of the present invention will be described next. FIG. 12 is a flowchart for exemplifying a process procedure performed by the control unit 35 in the display device 36 according to the third embodiment of the present invention. When having determined the posture to be taken by the subject 1 corresponding to the intra-organ reached position of the capsule endoscope 3 in the subject 1, the control unit 35 controls the display unit 12 to display the intra-organ reached position and the posture to be taken by the subject 1, and controls the notifying unit 34 to notify of the speech information indicating the posture to be taken by the subject 1. Other process procedures executed by the control unit 35 are substantially the same as the process procedures (see FIG. 7) of the control unit 25 in the display device 26 according to the second embodiment.

That is, as shown in FIG. 12, the control unit 35 acquires the in-vivo image of the subject 1 and the received field strength information via the communication unit 13, similarly to the above-described Steps S201 and S202 (Step S401), and calculates the capsule position based on the received field strength information acquired together with the in-vivo image (Step S402).

The control unit 35 determines whether the stagnant state of the capsule in the subject 1 continues for a predetermined time or longer (Step S403), similarly to the above-described Step S203, and when having determined that the stagnant state of the capsule continues for a predetermined time or longer (Yes at Step S403), confirms whether to change the posture of the subject 1 who has the stagnating capsule endoscope 3 in his internal organ (Step S404), similarly to the above-described Step S204. The control unit 35 further determines whether there is a posture change instruction of the subject 1 based on the check result of the posture change instruction similarly to the above-described Step S205 (Step S405).

When having determined that there is the posture change instruction of the subject 1 at Step S405 (Yes at Step S405), the control unit 35 determines whether the capsule endoscope 3 in the subject 1 reaches the predetermined intra-organ reached position (that is, position in large intestine, which is an internal organ to be observed) similarly to the above-described Steps S206 to S208.

That is, when there is the posture change instruction of the subject 1, the control unit 35 determines whether the capsule endoscope 3 has reached the ascending colon similarly to the above-described Step S206 (Step S406). When having determined that the capsule endoscope 3 has not reached the ascending colon (No at Step S406), the control unit 35 determines whether the capsule endoscope 3 has reached the transverse colon similarly to the above-described Step S207 (Step S407). When having determined that the capsule endoscope 3 has not reached the transverse colon (No at Step S407), the control unit 35 determines whether the capsule endoscope 3 has reached the descending colon similarly to the above-described Step S208 (Step S408).

On the other hand, when having determined that the capsule endoscope 3 has reached the ascending colon at Step S406 (Yes at Step S406), the control unit 35 sets the posture to be taken by the subject 1 as the Trendelenburg's position similarly to the above-described Step S209 (Step S409). When having determined that the capsule endoscope 3 has reached the transverse colon at Step S407 (Yes at Step S407), the control unit 35 sets the posture to be taken by the subject 1 as the left lateral decubitus position similarly to the above-described Step S210 (Step S410). When having determined that the capsule endoscope 3 has reached the descending colon at Step S408 (Yes at Step S408), the control unit 35 sets the posture to be taken by the subject 1 as the sitting position similarly to the above-described Step S211 (Step S411).

The control unit 35 controls the display unit 12 to display the intra-organ reached position of the capsule endoscope 3 in the subject 1 and the posture of the subject 1 similarly to the above-described Step S212, after setting the posture to be taken by the subject 1 by performing any one of process procedures at Steps S409 to S411 (Step S412).

The control unit 35 instructs the notifying unit 34 to notify of the posture to be taken by the subject 1 (Step S413). Specifically, the notification controller 35e generates speech information indicating the posture to be taken by the subject 1 determined by performing any one of process procedures of Steps S409 to S411, and controls the notifying unit 34 to notify of the generated speech information. In this case, the notification controller 35e controls the notifying unit 34 to notify of the speech information corresponding to the posture of the subject displayed at Step S412, that is, the posture of the subject 1 indicated by the posture image displayed on the examination-procedure display unit 12c (for example, speech information indicating the posture itself of the subject 1 or speech information indicating a content explaining the posture of the subject 1).

Then, the control unit 35 controls the display unit 12 to display the in-vivo images of the subject 1 acquired at Step S401 similarly to the above-described Step S213 (Step S414). Subsequently, the control unit 35 returns to Step S401 to repeat the process procedures at Step S401 and onwards.

When having determined that the stagnant state of the capsule does not continue for a predetermined time or longer at Step S403 (No at Step S403), or when having determined that there is no posture change instruction of the subject 1 at Step S405 (No at Step S405), or when having determined that the capsule endoscope 3 has not reached the descending colon at Step S408 (No at Step S408), the control unit 35 proceeds to Step S414 to repeat the process procedures at Step S414 and onwards.

Figure 13:
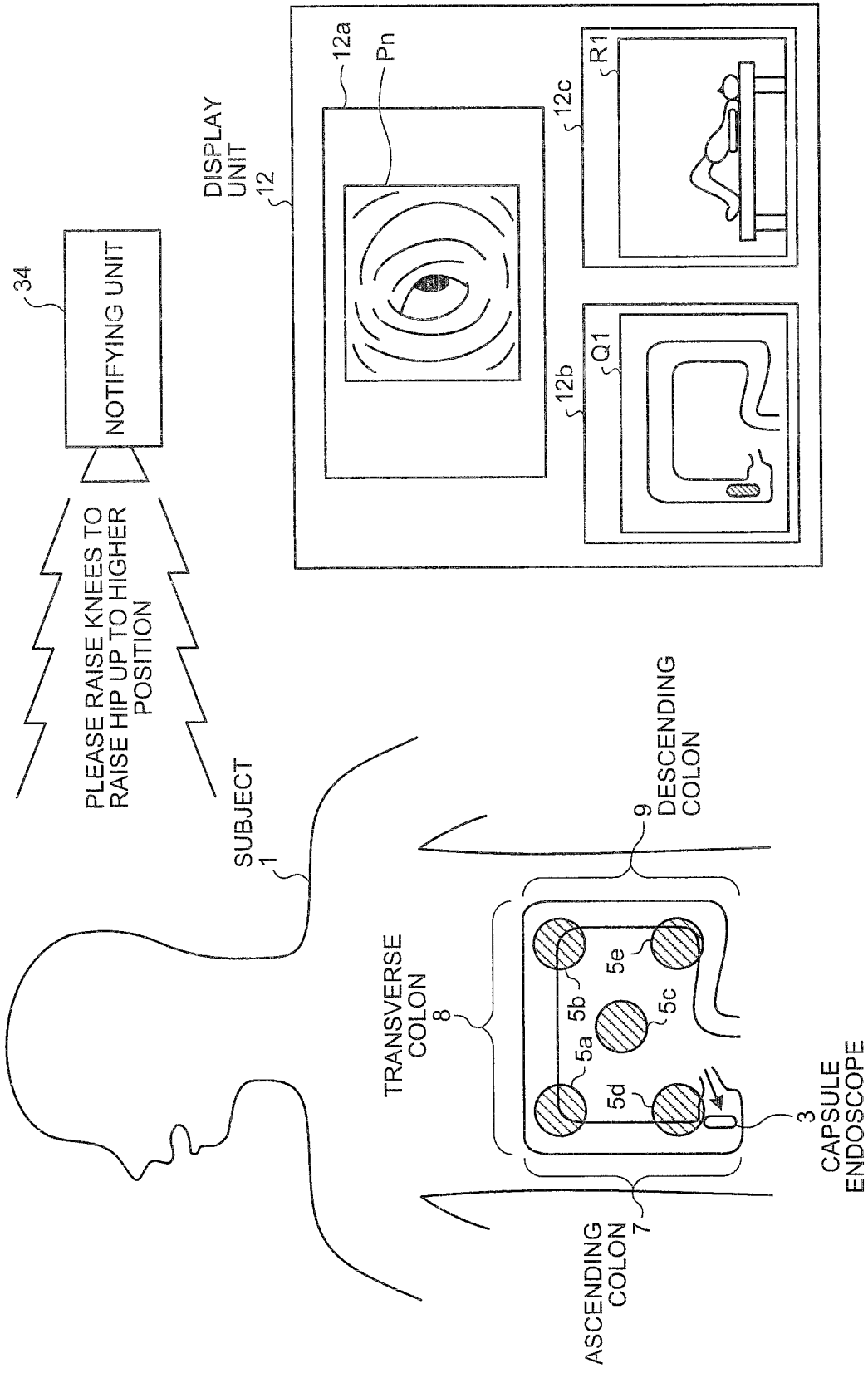
FIG. 13 is a schematic diagram for specifically explaining an operation of the control unit of the display device according to the third embodiment of the present invention.

An operation of the control unit 35 in the display device 36 according to the third embodiment of the present invention will be described next by exemplifying a case that the large intestine of the subject 1 is the observed region. FIG. 13 is a schematic diagram for specifically explaining an operation of the control unit 35 in the display device 36 according to the third embodiment of the present invention. The operation of the control unit 35 will be described below in detail with reference to FIG. 13.

Similarly to the second embodiment, the capsule endoscope 3 is swallowed from the mouth of the subject 1, and sequentially passes through the esophagus, stomach, and small intestine with peristaltic movements. While the capsule endoscope 3 sequentially advances inside the internal organs of the subject 1, the control unit 35 calculates a capsule position at the time of capturing the in-vivo image $P_n$, every time the in-vivo image $P_n$ captured by the capsule endoscope 3 is acquired, like the control unit 25 in the display device 26 according to the second embodiment.

If the stagnant state of the capsule does not continue for a predetermined time or longer (for example, longer than 5 seconds) in the subject 1, the control unit 35 sequentially displays the in-vivo images $P_n$ on the image display unit 12a without displaying the check window 22a, like the control unit 25 in the display device 26 according to the second embodiment.

On the other hand, if the capsule endoscope 3 in the subject 1 has reached the ascending colon and stagnates therein for a predetermined time or longer (for example, longer than 5 seconds), the control unit 35 determines that the stagnant state of the capsule continues for a predetermined time or longer in the ascending colon, like the control unit 25 in the display device 26 according to the second embodiment, and performs control to display the in-vivo images $P_n$ on the image display unit 12a and the check window 22a on the display unit 12. Further, when posture change instruction information corresponding to the selection button 22b in the check window 22a is input by the input unit 11, the control unit 35 interprets that there is a posture change instruction of the subject 1, and determines the posture to be taken by the subject 1 as the Trendelenburg's position corresponding to the ascending colon 7, which is the intra-organ reached position of the stagnating capsule endoscope.

When having determined the posture to be taken by the subject 1 as the Trendelenburg's position, the control unit 35 performs control to display the position image Q1 and the posture image R1 on the position display unit 12b and the examination-procedure display unit 12c, respectively. Subsequently, the control unit 35 controls the notifying unit 34 to notify of speech information indicating the posture to be taken by the subject 1 (Trendelenburg's position). Based on the control by the control unit 35, the notifying unit 34 notifies the subject 1 of speech information having a content explaining the posture to be taken by the subject 1 (Trendelenburg's position), for example, "Please raise knees to raise hip up to a higher position".

The subject 1 can easily understand the posture to be taken currently by notifying the subject 1 of such speech information by the notifying unit 34. Therefore, a user such as a doctor or nurse can have the subject 1 taken this posture (Trendelenburg's position) easily. When the subject 1 takes the Trendelenburg's position, the capsule endoscope 3 inside the ascending colon 7 smoothly advances inside the ascending colon 7 and reaches the transverse colon 8.

Thereafter, the control unit 35 performs control to display the check window 22a on the display unit 12 every time it is determined that the stagnant state of the capsule continues for a predetermined time or longer, like the control unit 25 in the display device 26 according to the second embodiment. That is, the check window 22a is displayed on the display unit 12 every time the capsule endoscope 3 continuously stagnates in the transverse colon 8 or the descending colon 9 of the subject 1 for a predetermined time or longer.

When the posture change instruction information corresponding to the selection button 22b in the check window 22a is input by the input unit 11, the control unit 35 determines the posture to be taken by the subject 1 corresponding to the intra-organ reached position of the capsule endoscope 3 in each time. Specifically, when the capsule endoscope 3 continuously stagnates in the transverse colon 8 for a predetermined time or longer, the control unit 35 determines the posture to be taken by the subject 1 as the left lateral decubitus position, and performs control to display the position image Q2 and the posture image R2 on the position display unit 12b and the examination-procedure display unit 12c, respectively. Subsequently, the control unit 35 controls the notifying unit 34 to notify of speech information indicating the posture to be taken by the subject 1 (left lateral decubitus position). On the other hand, when the capsule endoscope 3 continuously stagnates in the descending colon 9 for a predetermined time or longer, the control unit 35 determines the posture to be taken by the subject 1 as the sitting position, and performs control to display the position image Q3 and the posture image R3 on the position display unit 12b and the examination-procedure display unit 12c, respectively. Subsequently, the control unit 35 controls the notifying unit 34 to notify of speech information indicating the posture to be taken by the subject 1 (sitting position).

The notifying unit 34 can notify of the speech information indicating the posture to be taken by the subject 1 corresponding to the current intra-organ reached position, every time the intra-organ reached position of the capsule endoscope 3 in the subject 1 changes to the ascending colon, transverse colon, or descending colon, based on the control by the control unit 35. The subject 1 can easily understand the current posture to be taken according to the speech information from the notifying unit 34. Therefore, a user such as a doctor or nurse can have the subject 1 taken the posture corresponding to the current intra-organ reached position of the capsule endoscope 3 (that is, the posture accelerating smooth advancement of the capsule endoscope 3) easily. Thus, when the subject 1 sequentially changes the posture according to the speech information from the notifying unit 34, the capsule endoscope 3 in the subject 1 can smoothly advance in the ascending colon 7, the transverse colon 8, and the descending colon 9 sequentially.

As described above, according to the third embodiment of the present invention, the same functions as those of the second embodiment are provided, and the speech information indicating the posture to be taken by the subject is notified. Accordingly, the current posture to be taken corresponding to the intra-organ reached position of the capsule endoscope (that is, the posture accelerating smooth advancement of the capsule endoscope in the internal organs) can be easily ascertained by the subject. Further, the display device that can secure the same operations and effects as those of the second embodiment, and can have the subject taken the posture, which accelerates smooth advancement of the capsule endoscope in the internal organs, and the in-vivo information acquiring system using the same can be achieved.

Fourth Embodiment

A fourth embodiment of the present invention will be described below. In the second embodiment, the posture to be taken by the subject 1 is informed by displaying the posture image on the examination-procedure display unit 12c; however, in the fourth embodiment, the posture of the subject 1 is changed by driving a bed, on which the subject 1 is lying, according to the posture to be taken by the subject 1.

Figure 14:
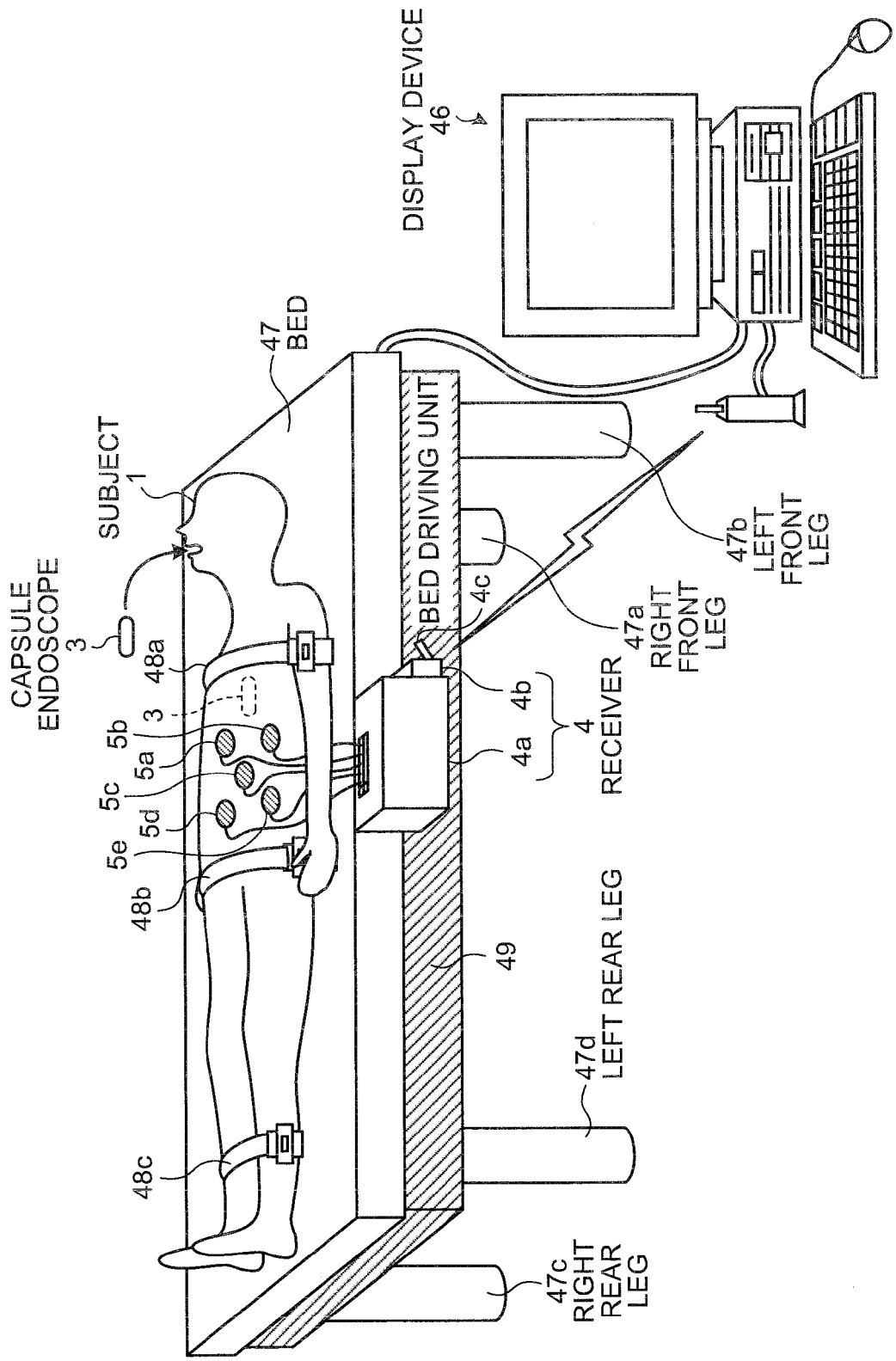
FIG. 14 is a configuration example of an in-vivo information acquiring system according to a fourth embodiment of the present invention.

FIG. 14 is a schematic diagram a configuration example of an in-vivo information acquiring system according to the fourth embodiment of the present invention. As shown in FIG. 14, the in-vivo information acquiring system according to the fourth embodiment has a driven bed 47 instead of the bed 2 in the in-vivo information acquiring system according to the second embodiment, and further has a bed driving unit 49 that drives the bed 47. The in-vivo information acquiring system according to the fourth embodiment further has a display device 46 instead of the display device 26 according to the second embodiment. Other configurations of the fourth embodiment are the same as those of the second embodiment, and like component parts are denoted by like reference numerals or letters.

The bed 47 is a driven bed that functions as a mounting unit that has mounted thereon the subject 1 who has the capsule endoscope 3 in his internal organ, and a leg length can be adjusted by an operation of the bed driving unit 49. Specifically, the bed 47 is equipped with the bed driving unit 49 that operates according to an instruction from the display device 46, and has a movable right front leg 47a, a left front leg 47b, a right rear leg 47c, and a left rear leg 47d, their respective leg lengths being adjustable. The leg lengths of the right front leg 47a, the left front leg 47b, the right rear leg 47c, and the left rear leg 47d are adjusted to a desired length, respectively, according to the operation of the bed driving unit 49. The bed 47 further has belts 48a, 48b, and 48c for restraining the subject 1. The subject 1 restrained by these belts 48a, 48b, and 48c is substantially secured (integrated) with respect to the bed 47.

The bed driving unit 49 functions as a drive that drives the bed 47 to change the posture of the subject 1. Specifically, the bed driving unit 49 is connected to, for example, a control unit (described later) of the display device 46 via a cable, and driven and controlled by the control unit of the display device 46. The bed driving unit 49 respectively drives the right front leg 47a, the left front leg 47b, the right rear leg 47c, and the left rear leg 47d, and adjusts the leg lengths of the right front leg 47a, the left front leg 47b, the right rear leg 47c, and the left rear leg 47d, respectively, to a desired length. The bed driving unit 49 changes the posture of the subject 1 mounted (restrained) on the bed 47 by adjusting the respective leg lengths of the bed 47.

Figure 15:
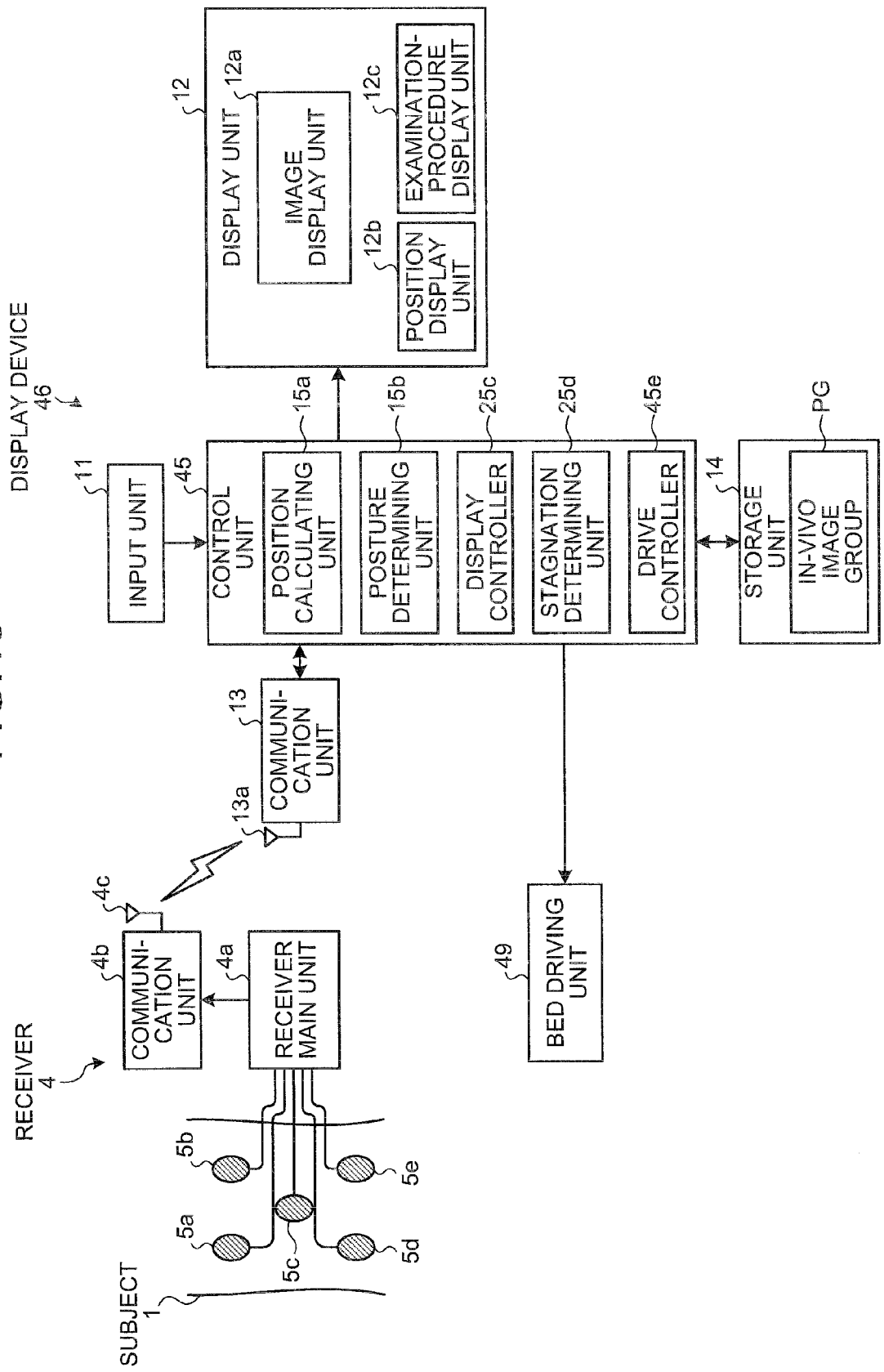
FIG. 15 is a block diagram for schematically depicting a configuration example of a display device according to the fourth embodiment of the present invention.

A configuration of the display device 46 according to the fourth embodiment of the present invention will be described next. FIG. 15 is a block diagram for schematically depicting a configuration example of the display device 46 according to the fourth embodiment of the present invention. As shown in FIG. 15, the display device 46 according to the fourth embodiment includes a control unit 45 instead of the control unit 25 in the display device 26 according to the second embodiment. The control unit 45 has a function for controlling the bed driving unit 49. Other configurations of the fourth embodiment are the same as those of the second embodiment, like component parts are denoted by like reference numerals or letters.

The control unit 45 controls the bed driving unit 49 to change the posture of the subject 1 on the bed 47, according to the posture to be taken by the subject 1 corresponding to the intra-organ reached position of the capsule endoscope 3 in the subject 1. Other functions of the control unit 45 are the same as those of the control unit 25 in the display device 26 according to the second embodiment. The control unit 45 includes the position calculating unit 15a, the posture determining unit 15b, the display controller 25c, and the stagnation determining unit 25d, like the control unit 25, and further includes a drive controller 45e that drives and controls the bed driving unit 49.

The drive controller 45e drives and controls the bed driving unit 49 so that the posture of the subject 1 on the bed 47 is changed according to the posture to be taken by the subject 1 corresponding to the intra-organ reached position of the capsule endoscope 3 inserted into the subject 1. Specifically, the drive controller 45e drives and controls the bed driving unit 49 according to the posture to be taken by the subject 1 determined by the posture determining unit 15b, so that the subject 1 on the bed 47 takes a posture corresponding to the posture to be taken by the subject 1. The drive controller 45e has pieces of leg length data of the bed 47 beforehand, corresponding to the respective postures (for example, Trendelenburg's position, left lateral decubitus position, and sitting position) of the subject 1 determined by the posture determining unit 15b. The drive controller 45e drives and controls the bed driving unit 49 based on the respective pieces of leg length data, so that the respective leg lengths of the right front leg 47a, the left front leg 47b, the right rear leg 47c, and the left rear leg 47d are adjusted to the lengths corresponding to the posture to be taken by the subject 1. Thus, the drive controller 45e drives and controls the bed driving unit 49 that changes the posture of the subject 1 on the bed 47 to a posture according to the posture determined by the posture determining unit 15b (that is, the posture to be taken by the subject 1).

The posture according to the posture determined by the posture determining unit 15b is a posture taken by the subject 1 on the bed 47 by driving the bed 47. Specifically, there can be mentioned a lower body elevated posture with a lower body being elevated as compared to an upper body of the subject 1, a right side elevated posture with the right side of the subject 1 being elevated as compared to the left side, and an upper body elevated posture with the upper body being elevated as compared to the lower body of the subject 1. In this case, the lower body elevated posture corresponds to the Trendelenburg's position, the right side elevated posture corresponds to the left lateral decubitus position, and the upper body elevated posture corresponds to the sitting position.

Figure 16:
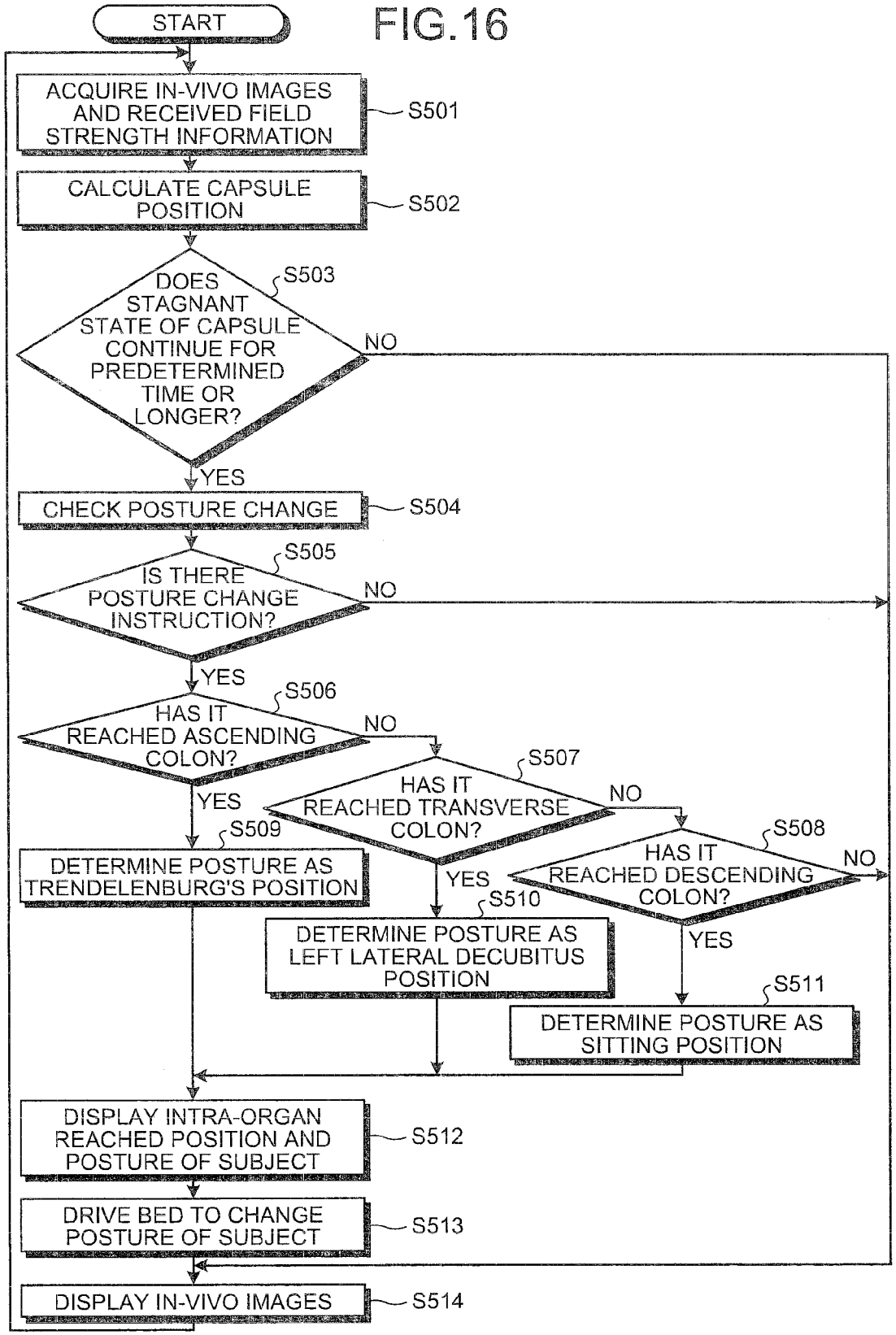
FIG. 16 is a flowchart for exemplifying a process procedure performed by a control unit of the display device according to the fourth embodiment of the present invention.

An operation of the control unit 45 in the display device 46 according to the fourth embodiment of the present invention will be described next. FIG. 16 is a flowchart for exemplifying a process procedure performed by the control unit 45 in the display device 46 according to the fourth embodiment of the present invention. When the posture to be taken by the subject 1 is determined corresponding to the intra-organ reached position of the capsule endoscope 3 in the subject 1, the control unit 45 controls the display unit 12 to display the intra-organ reached position and the posture to be taken by the subject 1. Further, the control unit 45 performs drive control of the bed driving unit 49 according to the posture to be taken by the subject 1, so that the subject 1 on the bed 47 takes a posture according to the posture determined by the posture determining unit 15b corresponding to the intra-organ reached position of the capsule endoscope 3. Other parts of the process procedures executed by the control unit 45 are substantially the same as those (see FIG. 7) of the control unit 25 in the display device 26 according to the second embodiment.

That is, as shown in FIG. 16, the control unit 45 acquires the in-vivo images of the subject 1 and the received field strength information via the communication unit 13 similarly to the above-described Steps S201 and S202 (Step S501), and calculates the capsule position based on the received field strength information acquired together with the in-vivo images (Step S502).

The control unit 45 then determines whether the stagnant state of the capsule continues for a predetermined time or longer in the subject 1 (Step S503). When having determined that the stagnant state of the capsule continues for a predetermined time or longer (Yes at Step S503), the control unit 45 confirms whether to change the posture of the subject 1 who has the stagnating capsule endoscope 3 in his internal organ similarly to the above-described Step S204 (Step S504). The control unit 45 then determines whether there is a posture change instruction of the subject 1 based on the check result of the posture change instruction similarly to the above-described Step S205 (Step S505).

When having determined that there is the posture change instruction of the subject 1 at Step S505 (Yes at Step S505), the control unit 45 determines whether the capsule endoscope 3 in the subject 1 has reached a predetermined intra-organ reached position (that is, a position in large intestine, which is the organ to be observed) similarly to the above-described Steps S206 to S208.

That is, when there is the posture change instruction of the subject 1, the control unit 45 determines whether the capsule endoscope 3 has reached the ascending colon similarly to the above-described Step S206 (Step S506). When having determined that the capsule endoscope 3 has not reached the ascending colon (No at Step S506), the control unit 45 determines whether the capsule endoscope 3 has reached the transverse colon similarly to the above-described Step S207 (Step S507). When having determined that the capsule endoscope 3 has not reached the transverse colon (No at Step S507), the control unit 45 determines whether the capsule endoscope 3 has reached the descending colon similarly to the above-described Step S208 (Step S508).

On the other hand, when having determined that the capsule endoscope 3 has reached the ascending colon at Step S506 (Yes at Step S506), the control unit 45 sets the posture to be taken by the subject 1 as the Trendelenburg's position similarly to the above-described Step S209 (Step S509). When having determined that the capsule endoscope 3 has reached the transverse colon at Step S507 (Yes at Step S507), the control unit 45 sets the posture to be taken by the subject 1 as the left lateral decubitus position similarly to the above-described Step S210 (Step S510). When having determined that the capsule endoscope 3 has reached the descending colon at Step S508 (Yes at Step S508), the control unit 45 sets the posture to be taken by the subject 1 as the sitting position similarly to the above-described Step S211 (Step S511).

The control unit 45 controls the display unit 12 to display the intra-organ reached position of the capsule endoscope 3 in the subject 1 and the posture of the subject 1 similarly to the above-described Step S212, after setting the posture to be taken by the subject 1 by performing any one of process procedures at Steps S509 to S511 (Step S512).

Thereafter, the control unit 45 drives the bed 47 so that the subject 1 on the bed 47 takes the posture to be taken by the subject 1, thereby changing the posture of the subject 1 (Step S513). Specifically, the drive controller 45e drives and controls the bed driving unit 49 based on the preset pieces of leg length data of the bed 47, and adjusts the respective leg lengths of the right front leg 47a, the left front leg 47b, the right rear leg 47c, and the left rear leg 47d of the bed 47 corresponding to the posture to be taken by the subject 1 determined by the posture determining unit 15b by performing any one of process procedures of Steps S509 to S511. The drive controller 45e changes the posture of the subject 1 on the bed 47 so that the subject 1 takes the posture according to the posture determined by the posture determining unit 15b (that is, the posture to be taken by the subject 1) by adjusting the respective leg lengths of the bed 47.

The control unit 45 then controls the display unit 12 to display the in-vivo images of the subject 1 acquired at Step S501 similarly to the above-described Step S213 (Step S524). Thereafter, the control unit 45 returns to Step S501 to repeat the process procedures at Step S501 and onwards.

When having determined that the stagnant state of the capsule does continue for a predetermined time or longer at Step S503 (No at Step S503), when having determined that there is no posture change instruction of the subject 1 at Step S505 (No at Step S505), or when having determined that the capsule endoscope 3 has not yet reached the descending colon at Step S508 (No at Step S508), the control unit 45 proceeds to Step S514 to repeat the process procedures at Step S514 and onwards.

Figure 17:
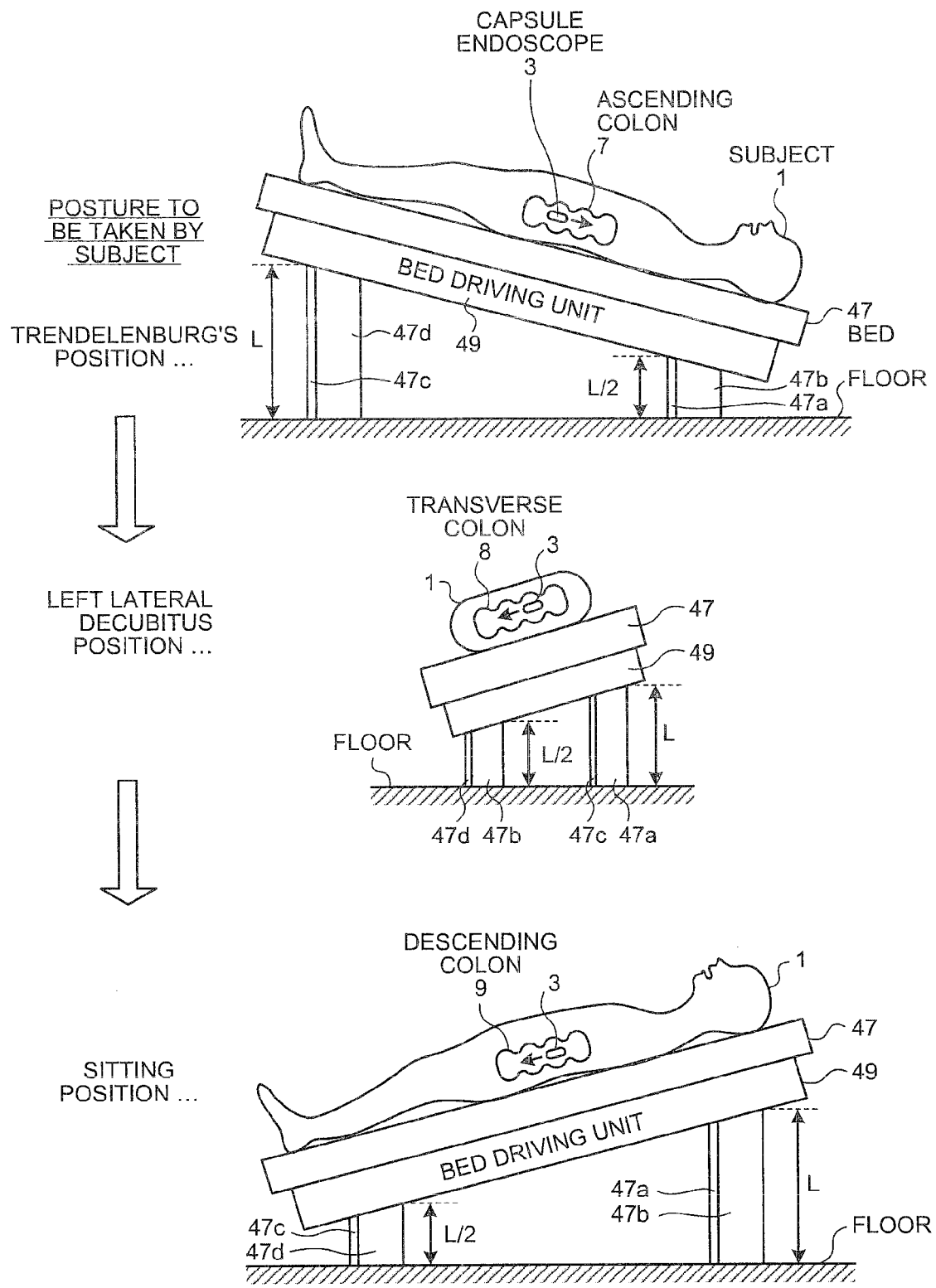
FIG. 17 is a schematic diagram for specifically explaining an operation of the control unit of the display device according to the fourth embodiment of the present invention.

An operation of the control unit 45 in the display device 46 according to the fourth embodiment of the present invention will be specifically described next by exemplifying a case that large intestine of the subject 1 is an observed region. FIG. 17 is a schematic diagram for specifically explaining the operation of the control unit 45 in the display device 46 according to the fourth embodiment of the present invention. FIG. 18 is an example of the pieces of leg length data of the bed 47 corresponding to the posture to be taken by the subject 1. The respective pieces of leg length data of the bed 47 shown in FIG. 18 show an example combined corresponding to the respective postures to be taken by the subject 1 and do not limit the present invention. The operation of the control unit 45 will be specifically described below with reference to FIGS. 17 and 18.

Similarly to the second embodiment, the capsule endoscope 3 is swallowed from the mouth of the subject 1, and sequentially passes through esophagus, stomach, and small intestine with peristaltic movements. While the capsule endoscope 3 sequentially advances inside the internal organ of the subject 1, the control unit 45 calculates a capsule position at the time of capturing the in-vivo image $P_n$, every time the in-vivo image $P_n$ captured by the capsule endoscope 3 is acquired, like the control unit 25 in the display device 26 according to the second embodiment.

Further, if the stagnant state of the capsule does not continue for a predetermined time or longer (for example, longer than 5 seconds) in the subject 1, the control unit 45 sequentially displays the in-vivo images $P_n$ on the image display unit 12a without displaying the check window 22a, like the control unit 25 in the display device 26 according to the second embodiment.

On the other hand, if the capsule endoscope 3 in the subject 1 has reached the ascending colon and stagnates therein for a predetermined time or longer (for example, longer than 5 seconds), the control unit 45 determines that the stagnant state of the capsule continues for a predetermined time or longer in the ascending colon, like the control unit 25 in the display device 26 according to the second embodiment, and performs control to display the in-vivo images $P_n$ on the image display unit 12a and the check window 22a on the display unit 12. Further, when posture change instruction information corresponding to the selection button 22b in the check window 22a is input by the input unit 11, the control unit 45 interprets that there is a posture change instruction of the subject 1. In this case, the posture determining unit 15b determines the posture to be taken by the subject 1 as the Trendelenburg's position corresponding to the ascending colon 7, which is the intra-organ reached position of the stagnating capsule endoscope.

When having determined the posture to be taken by the subject 1 as the Trendelenburg's position, the control unit 45 performs control to display the position image Q1 and the posture image R1 on the position display unit 12b and the examination-procedure display unit 12c, respectively. Subsequently, the control unit 45 makes the subject 1 on the bed 47 take the lower body elevated posture according to the determined posture to be taken by the subject 1 (Trendelenburg's position). In this case, the drive controller 45e refers to a data table shown in FIG. 18 to perform the drive control of the bed driving unit 49 to adjust the bed 47 to the respective leg lengths corresponding to the posture to be taken by the subject 1 determined by the posture determining unit 15b (Trendelenburg's position).

The bed driving unit 49 adjusts the respective leg lengths of the right front leg 47a and the left front leg 47b of the bed 47 to L/2 (L is a predetermined constant) and adjusts the respective leg lengths of the right rear leg 47c and the left rear leg 47d to L, based on the drive control by the drive controller 45e. Thus, the bed 47 with the respective leg lengths being adjusted makes the subject 1 take the lower body elevated posture according to the Trendelenburg's position, which is the posture to be taken when the intra-organ reached position of the capsule endoscope 3 is the ascending colon 7. In this manner, when the subject 1 on the bed takes the lower body elevated posture, the capsule endoscope 3 in the ascending colon 7 smoothly advances through the ascending colon 7 and reaches the transverse colon 8.

Thereafter, the control unit 45 performs control to display the check window 22a on the display unit 12 every time the control unit 45 determines that the stagnant state of the capsule continues for a predetermined time or longer, like the control unit 25 in the display device 26 according to the second embodiment. That is, the check window 22a is displayed on the display unit 12 every time the capsule endoscope 3 stagnates in the transverse colon 8 or the descending colon 9 of the subject 1 for a predetermined time or longer.

When the posture change instruction information corresponding to the selection button 22b in the check window 22a is input by the input unit 11, the control unit 45 determines the posture to be taken by the subject 1 corresponding to the intra-organ reached position of the capsule endoscope 3 in each case.

Specifically, when the capsule endoscope 3 stagnates continuously for a predetermined time or longer in the transverse colon 8, the posture determining unit 15b determines the posture to be taken by the subject 1 as the left lateral decubitus position. In this case, the display controller 25c performs control to display the position image Q2 and the posture image R2 on the position display unit 12b and the examination-procedure display unit 12c, respectively. Further, the drive controller 45e refers to the data table shown in FIG. 18 to perform the drive control of the bed driving unit 49 to adjust the bed 47 to the respective leg lengths corresponding to the posture to be taken by the subject 1 determined by the posture determining unit 15b (left lateral decubitus position).

The bed driving unit 49 adjusts the respective leg lengths of the left front leg 47b and the left rear leg 47d of the bed 47 to L/2 and adjusts the respective leg lengths of the right front leg 47a and the right rear leg 47c to L, based on the drive control by the drive controller 45e. Thus, the bed 47 with the respective leg lengths being adjusted makes the subject 1 take the right side elevated posture according to the left lateral decubitus position, which is the posture to be taken when the intra-organ reached position of the capsule endoscope 3 is the transverse colon 8.

On the other hand, when the capsule endoscope 3 stagnates continuously for a predetermined time or longer in the descending colon 9, the posture determining unit 15b determines the posture to be taken by the subject 1 as the sitting position. In this case, the display controller 25c performs control to display the position image Q3 and the posture image R3 on the position display unit 12b and the examination-procedure display unit 12c, respectively. Further, the drive controller 45e refers to the data table shown in FIG. 18 to perform the drive control of the bed driving unit 49 to adjust the bed 47 to the respective leg lengths corresponding to the posture to be taken by the subject 1 determined by the posture determining unit 15b (sitting position).

The bed driving unit 49 adjusts the respective leg lengths of the right front leg 47a and the left front leg 47b of the bed 47 to L and adjusts the respective leg lengths of the right rear leg 47c and the left rear leg 47d to L/2, based on the drive control by the drive controller 45e. Thus, the bed 47 with the respective leg lengths being adjusted makes the subject 1 take the upper body elevated posture according to the sitting position, which is the posture to be taken when the intra-organ reached position of the capsule endoscope 3 is the descending colon 9.

Based on the control by the control unit 45, the bed driving unit 49 can drive the bed 47 so that the subject 1 takes the posture (lower body elevated posture, right side elevated posture, and upper body elevated posture) according to the posture to be taken by the subject 1 corresponding to the current intra-organ reached position, every time the intra-organ reached position of the capsule endoscope 3 in the subject 1 changes to the ascending colon, the transverse colon, or the descending colon. A user such as a doctor or nurse can have the subject 1 automatically taken the posture corresponding to the current intra-organ reached position of the capsule endoscope 3 (that is, the posture that accelerates smooth advancement of the capsule endoscope 3) according to the drive by the bed driving unit 49. Thus, when the posture of the subject 1 on the bed 47 is sequentially changed by the bed driving unit 49 based on the control by the drive controller 45e, the capsule endoscope 3 in the subject 1 can smoothly advance in the ascending colon 7, the transverse colon 8, and the descending colon 9 sequentially.

As described above, the fourth embodiment of the present invention has the same functions as those of the second embodiment, and the posture of the subject on the bed is changed to a posture corresponding to the intra-organ reached position of the capsule endoscope by providing the driven bed on which the subject lies, and by controlling the drive of the bed according to the posture to be taken by the subject. Accordingly, the current posture to be taken corresponding to the intra-organ reached position of the capsule endoscope (that is, the posture accelerating smooth advancement of the capsule endoscope in the internal organ) can be taken by the subject automatically. Further, the display device that can secure the same operations and effects as those of the second embodiment, and can have the subject taken the posture, which accelerates smooth advancement of the capsule endoscope in the internal organs, and the in-vivo information acquiring system using the same can be achieved.

According to the fourth embodiment of the present invention, the respective leg lengths of the right front leg 47a, the left front leg 47b, the right rear leg 47c, and the left rear leg 47d of the bed 47 are changed based on the drive control by the drive controller 45e, thereby changing inclination of the bed 47 to change the posture of the subject 1. However, the inclination of the bed 47 can be changed by rotating a shaft capable of rotating the bed 47 to change the posture of the subject 1.

Figure 19:
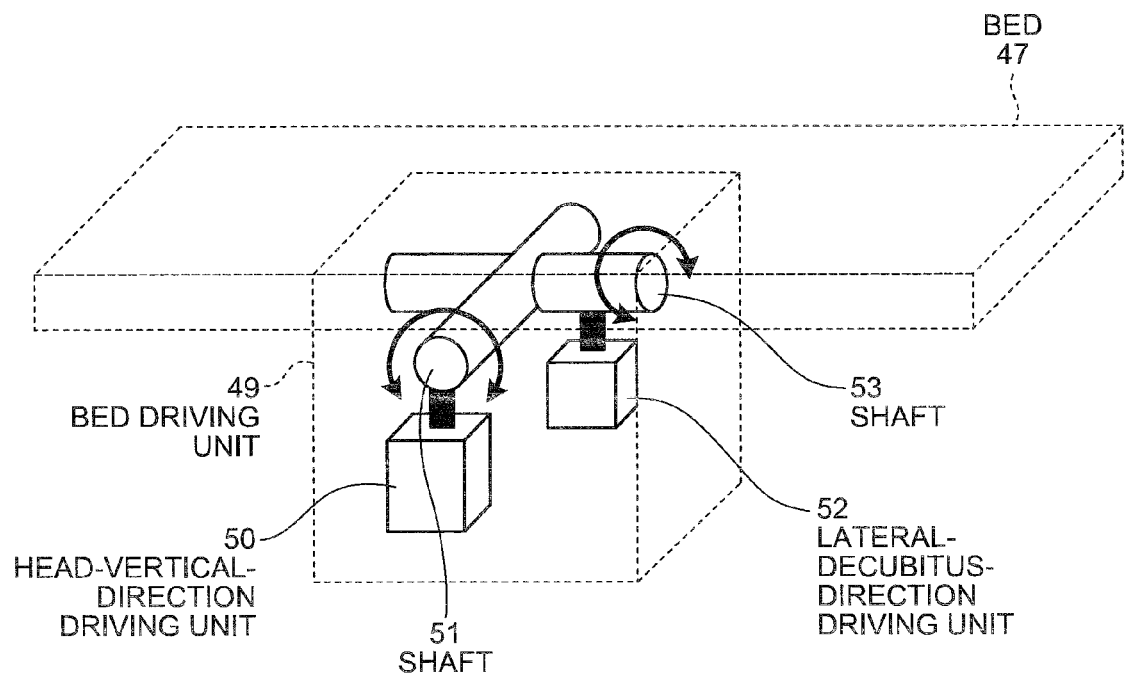
FIG. 19 is a schematic diagram of a modified example 1 of a driven bed in the in-vivo information acquiring system according to the fourth embodiment of the present invention.

FIG. 19 is a schematic diagram of a modified example 1 of the driven bed in the in-vivo information acquiring system according to the fourth embodiment of the present invention. In FIG. 19, the bed 47 according to the modified example 1 is shown, with the bed 47 and the bed driving unit 49 being shown by a dotted line, to facilitate explanations of an internal configuration of the bed driving unit 49 provided in the bed 47. As shown in FIG. 19, the bed 47 according to the modified example 1 is provided with the bed driving unit 49 that changes the inclination of the bed 47 due to rotation of the shaft, instead of changing the leg lengths. The bed driving unit 49 in the modified example 1 rotatably supports the bed 47, and includes a head-vertical-direction driving unit 50 and a shaft 51 for inclining the bed 47 in a vertical direction of the head of the subject 1, and a lateral-decubitus-direction driving unit 52 and a shaft 53 for inclining the bed 47 in a left and right direction (lateral decubitus direction) of the subject 1.

The shaft 51 inclines (rotates) the bed 47 in the vertical direction of the head of the subject 1, who lies on the bed 47, and is connected to the bed 47 and the head-vertical-direction driving unit 50. The head-vertical-direction driving unit 50 drives based on the control by the drive controller 45e, to rotate the shaft 51 in the vertical direction of the head indicated by an arrow in FIG. 19. The head-vertical-direction driving unit 50 rotates the shaft 51 to rotate the bed 47 in the vertical direction of the head of the subject 1, and as a result, changes the inclination of the bed 47 with respect to the vertical direction of the head of the subject 1 (that is, in a head-feet direction of the subject 1). The head-vertical-direction driving unit 50 changes the posture of the subject 1 on the bed 47 to the Trendelenburg's position or sitting position, due to the inclination change of the bed 47 in the vertical direction of the head.

The shaft 53 inclines (rotates) the bed 47 in the lateral decubitus direction of the subject 1, who lies on the bed 47, and is connected to the bed 47 and the lateral-decubitus-direction driving unit 52. The lateral-decubitus-direction driving unit 52 drives based on the control by the drive controller 45e, to rotate the shaft 53 in the lateral decubitus direction indicated by the arrow in FIG. 19. The lateral-decubitus-direction driving unit 52 rotates the shaft 53 to rotate the bed 47 in the lateral decubitus direction of the subject 1, and as a result, changes the inclination of the bed 47 with respect to the lateral decubitus direction of the subject 1 (that is, in a left-right direction of the subject 1). The lateral-decubitus-direction driving unit 52 changes the posture of the subject 1 on the bed 47 to the left lateral decubitus position or right lateral decubitus position, due to the inclination change of the bed 47 in the lateral decubitus direction.

On the other hand, in the fourth embodiment, the respective leg lengths of the right front leg 47a, the left front leg 47b, the right rear leg 47c, and the left rear leg 47d of the bed 47 are changed based on the drive control by the drive controller 45e, thereby changing the inclination of the bed 47 to change the posture of the subject 1. However, the bed 47 can be rotated with a mode in which a subject lying surface of the bed 47 is directed vertically upward.

Figure 20:
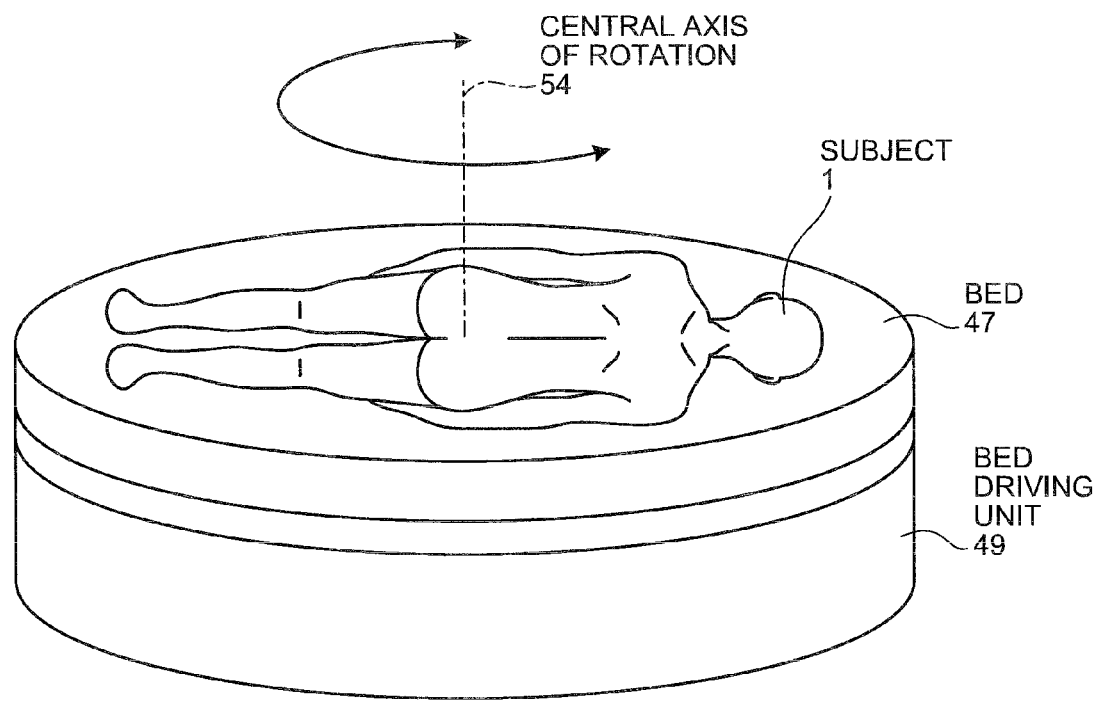
FIG. 20 is a schematic diagram of a modified example 2 of the driven bed in the in-vivo information acquiring system according to the fourth embodiment of the present invention.

FIG. 20 is a schematic diagram of a modified example 2 of the driven bed in the in-vivo information acquiring system according to the fourth embodiment of the present invention. In FIG. 20, the bed 47 according to the modified example 2 and the bed driving unit 49 that rotates the bed 47 are shown. As shown in FIG. 20, the bed 47 according to the modified example 2 is provided with the bed driving unit 49 that rotates the bed 47 with the mode in which the subject lying surface of the bed 47 is directed vertically upward, instead of changing the leg lengths. Specifically, the bed driving unit 49 in the modified example 2 rotatably supports the bed 47, and drives based on the control by the drive controller 45e, to rotate the bed 47 centering on a central axis of rotation 54 shown in FIG. 20. The bed driving unit 49 rotates the bed 47 in this manner, to rotate the subject 1 on the bed 47 together with the bed 47. In this case, the capsule endoscope 3 inserted into an internal organ (for example, inside of a stomach) of the subject 1 sequentially captures in-vivo images within a field of view, which changes with the rotation of the subject 1, while floating in a liquid such as water inside the internal organ, and as a result, captures the in-vivo images in a wide range in the internal organ. The user can comprehensively observe inside of the internal organs of the subject 1 by displaying the in-vivo images captured by the capsule endoscope 3 on the image display unit 12a (see FIG. 15, etc.) of the display unit 12.

Observation of the inside of the stomach of the subject 1 using the in-vivo images sequentially captured by the capsule endoscope 3 while changing the visual field with the rotation of the bed 47 (that is, rotation of the subject 1) will be described with reference to FIGS. 21 to 26 by exemplifying a case that the capsule endoscope 3 is inserted into the stomach of the subject 1 on the bed 47 according to the modified example 2.

First, the subject 1, who takes a predetermined posture (for example, left lateral decubitus position) on the bed 47, orally ingests the capsule endoscope 3 and a small amount of water. In this case, the capsule endoscope 3 captures the in-vivo images of the esophagus, while passing through the esophagus of the subject 1. In the modified example 2, a specific gravity of the capsule endoscope 3 is equal to or less than that of water (=1). The external display unit 12 displays the in-vivo images captured by the capsule endoscope 3 on the image display unit 12a, and the user observes the esophagus of the subject 1, using the in-vivo images displayed on the image display unit 12a.

When having confirmed that the capsule endoscope 3 has reached inside of the stomach of the subject 1 based on the calculation result of the position calculating unit 15a (that is, when the display unit 12 displays in-vivo images of the stomach of the subject 1 on the image display unit 12a), the external control unit 45 (see FIG. 15) controls the examination-procedure display unit 12c to display a posture image for instructing the subject 1 to take the right lateral decubitus position. The user has the subject 1 taken the right lateral decubitus position based on the posture image.

Thereafter, when having confirmed that the capsule endoscope 3 has reached a pylorus of the stomach based on the calculation result of the position calculating unit 15a (that is, when the display unit 12 displays the in-vivo images of the pylorus of the subject 1 on the image display unit 12a), the control unit 45 determines an amount of water and a posture of the subject 1 that make it possible to observe an angulus ventriculi based on the size of the pylorus and position information of the capsule, and controls the examination-procedure display unit 12c to display this determination result. In this case, the display unit 12 displays information indicating a recommended movement to be performed by the subject 1 (for example, "sitting position, no additional quantity") on the examination-procedure display unit 12c.

Next, when having confirmed that the capsule endoscope 3 has reached the angulus ventriculi of the subject 1 based on the calculation result of the position calculating unit 15a (that is, when the display unit 12 displays the in-vivo images of the angulus ventriculi of the subject 1 on the image display unit 12a), the control unit 45 controls the examination-procedure display unit 12c to display a posture image for instructing the subject 1 to take the right lateral decubitus position. The user has the subject 1 taken the right lateral decubitus position based on the posture image.

Figure 21:
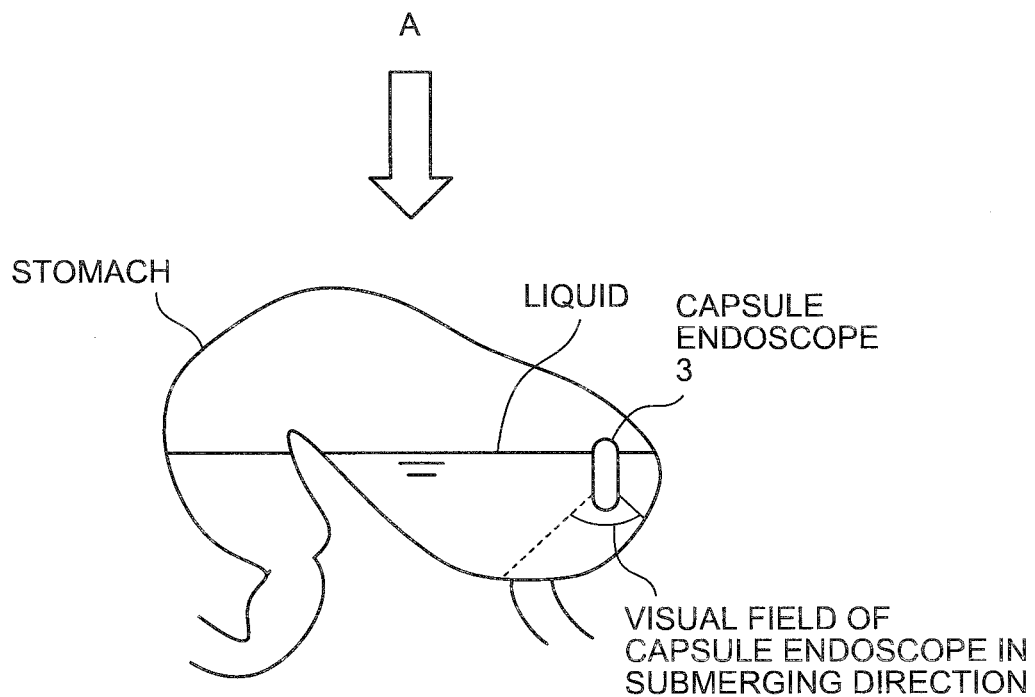
FIG. 21 is a schematic diagram of a stomach of a subject shown in FIG. 20 viewed from a back side.
Figure 22:
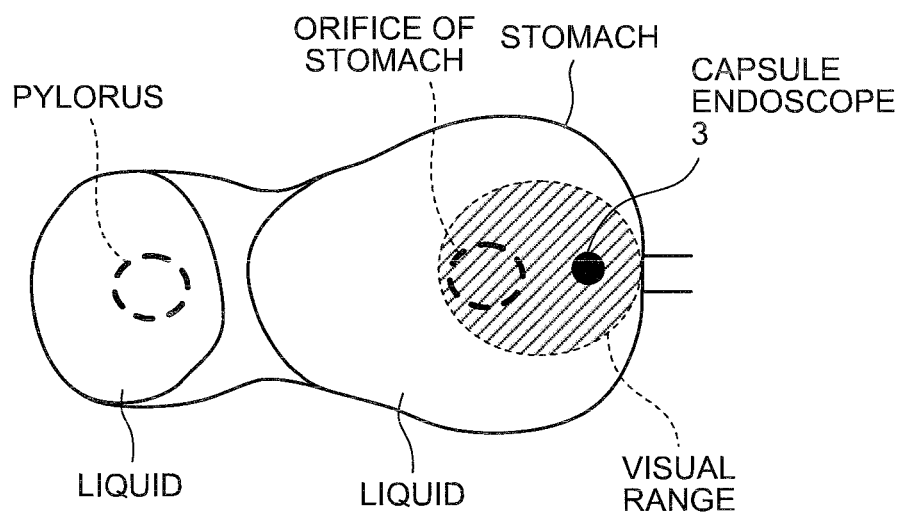
FIG. 22 is a schematic diagram of a stomach of a subject shown in FIG. 21 viewed from an A-side.
Figure 23:
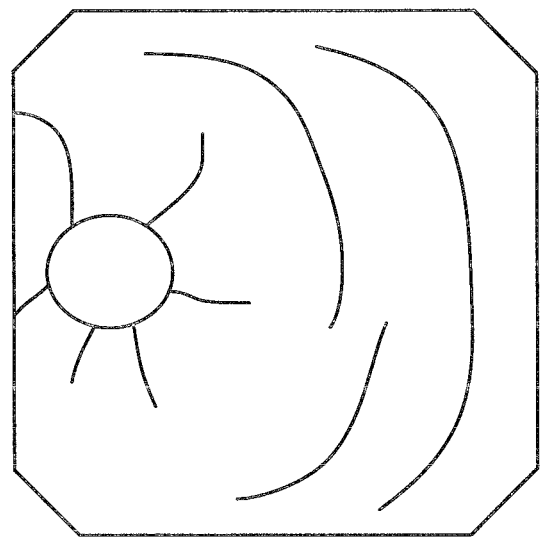
FIG. 23 is a schematic diagram of an example of an in-vivo image captured by a capsule endoscope shown in FIG. 22.

Thereafter, when having confirmed that the capsule endoscope 3 has reached an orifice of the stomach based on the calculation result of the position calculating unit 15a (that is, when the display unit 12 displays the in-vivo images of the orifice of the subject 1 on the image display unit 12a), the control unit 45 determines an appropriate amount of water based on an appearance of the orifice and the position information of the capsule, and controls the examination-procedure display unit 12c to display this determination result. In this case, if the subject 1 needs to ingest water additionally, the display unit 12 displays information indicating an additional amount of water on the examination-procedure display unit 12c. In this state, for example, as shown in FIGS. 21 and 22, the capsule endoscope 3 in the subject 1 captures the in-vivo images while floating in the water near the orifice of the stomach. The in-vivo images of the orifice captured by the capsule endoscope 3 (see FIG. 23) are displayed on the image display unit 12a of the display unit 12.

In this state, the control unit 45 controls the display unit 12 to display information instructing to rotate the bed 47 mounting the subject 1 thereon by 360 degrees. Under control of the control unit 45, the display unit 12 displays rotation instructing information of the bed 47 on the examination-procedure display unit 12c. The user operates the input unit 11 to rotate the bed 47 according to the information (rotation instruction) displayed on the examination-procedure display unit 12c. In this case, the bed driving unit 49 shown in FIG. 20 rotates the bed 47 by 360 degrees, centering on the central axis of rotation 54.

The control unit 45 may automatically control the rotation of the bed 47 instead of displaying the rotation instructing information of the bed 47 on the examination-procedure display unit 12c of the display unit 12. In this case, the drive controller 45e controls the bed driving unit 49 at a timing when the capsule endoscope 3 in the stomach has reached a predetermined position (for example, near the orifice as shown in FIGS. 21 and 22), to rotate the bed 47 centering on the central axis of rotation 54 shown in FIG. 20.

Figure 24:
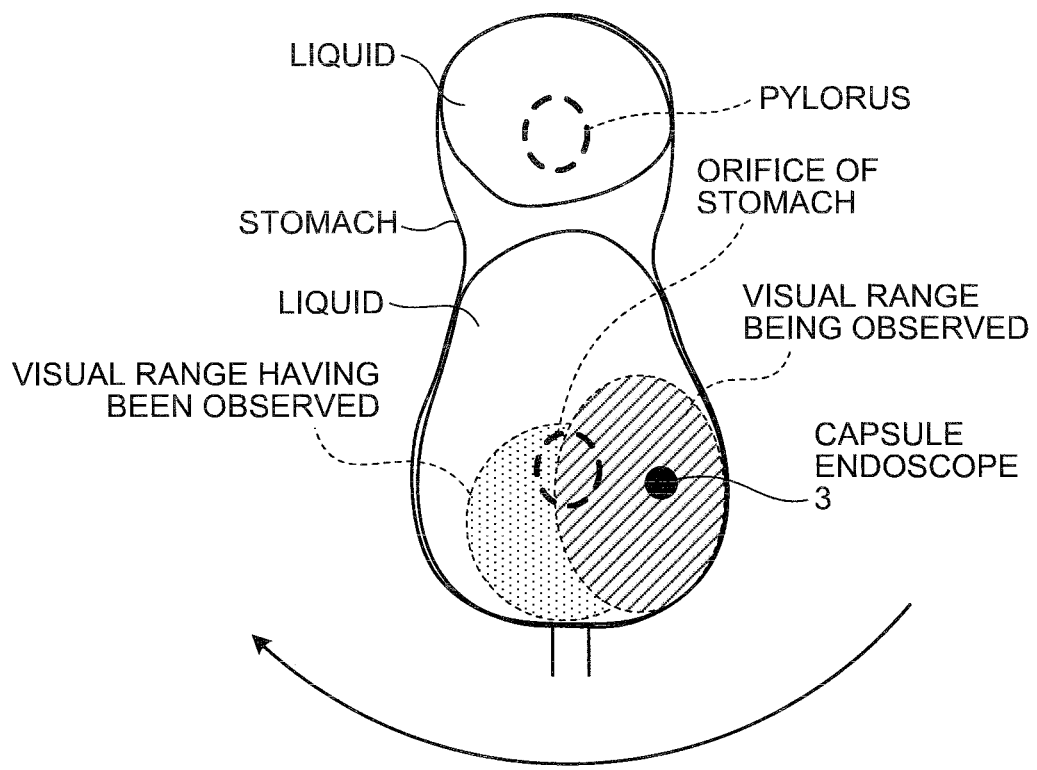
FIG. 24 is a schematic diagram of a stomach when a bed is rotated by 90 degrees to the right from a state shown in FIG. 22.
Figure 25:
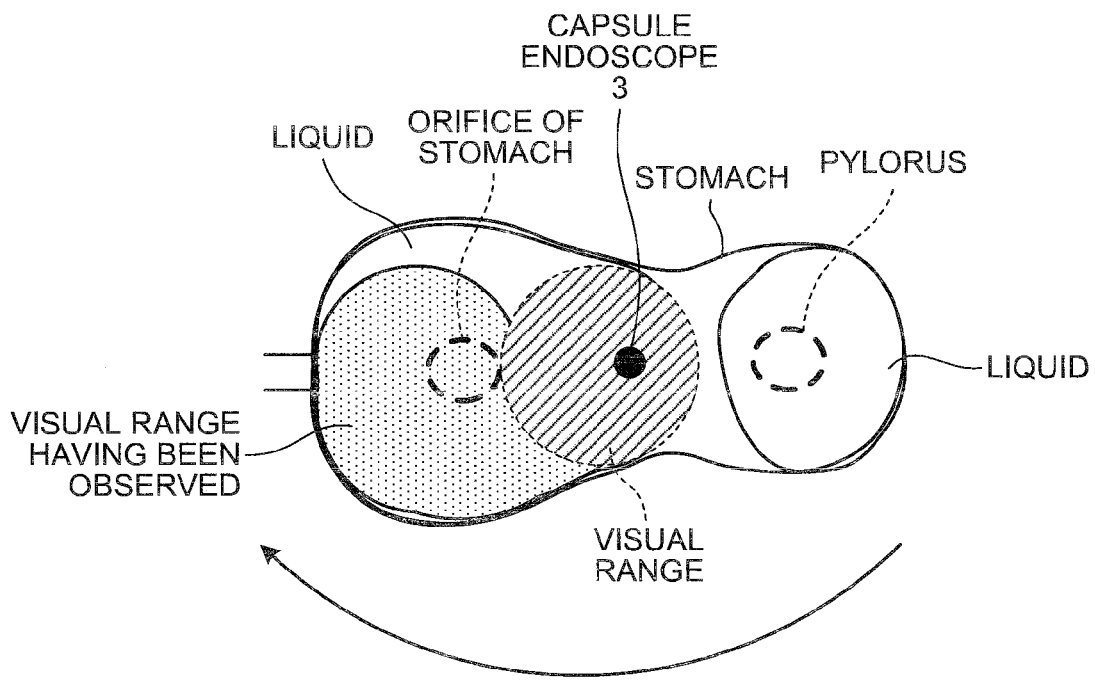
FIG. 25 is a schematic diagram of a stomach when a bed is rotated by 180 degrees to the right from the state shown in FIG. 22.
Figure 26:
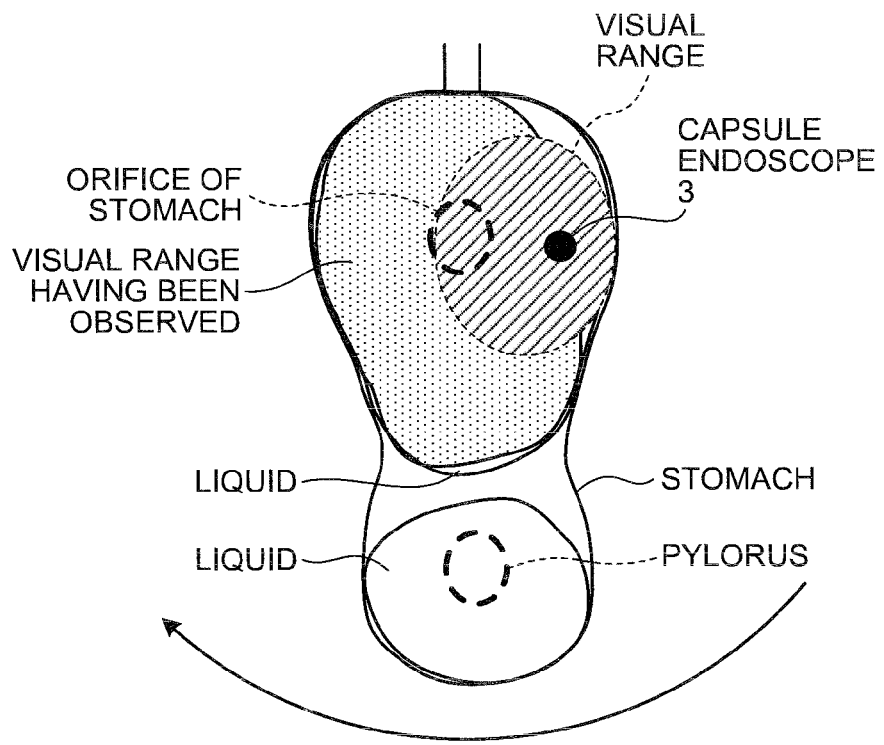
FIG. 26 is a schematic diagram of a stomach when a bed is rotated by 270 degrees to the right from the state shown in FIG. 22.

In the state where the bed 47 rotates by 360 degrees, the capsule endoscope 3 in the stomach tries to stay at a position before the rotation, while floating in the liquid such as water. A relative position between the stomach of the subject 1 and the capsule endoscope 3 changes with the rotation of the bed 47 with respect to the capsule endoscope 3. As a result, the capsule endoscope 3 in the stomach sequentially captures the in-vivo images, as shown in FIGS. 24 to 26, while changing the field of view (observation range). The in-vivo images sequentially captured by the capsule endoscope 3 are sequentially displayed on the image display unit 12a of the display unit 12.

The control unit 45 then determines whether the bed 47 has been rotated by 360 degrees, and when the bed 47 has not been rotated by 360 degrees, the rotation of the bed 47 is continued. On the other hand, when the bed 47 has been rotated by 360 degrees, the control unit 45 controls the examination-procedure display unit 12c to display a posture image for instructing the subject 1 to take the left lateral decubitus position. The user has the subject 1 taken the left lateral decubitus position based on the posture image.

After the subject 1 takes the left lateral decubitus position on the bed 47, the control unit 45 controls the display unit 12 to display information instructing to rotate the bed 47 mounting the subject 1 thereon by 360 degrees. Under control of the control unit 45, the display unit 12 displays the rotation instructing information of the bed 47 on the examination-procedure display unit 12c. The user operates the input unit 11 to rotate the bed 47 according to the information (rotation instruction) displayed on the examination-procedure display unit 12c. In this case, the bed driving unit 49 shown in FIG. 20 rotates the bed 47 by 360 degrees, centering on the central axis of rotation 54. As a result, the capsule endoscope 3 in the stomach sequentially captures the in-vivo images of an inner wall of the stomach, while changing the field of view in a state of floating in the liquid in the stomach, similarly to the case of the right lateral decubitus position.

In the case of the left lateral decubitus position as well, the control unit 45 may automatically control the rotation of the bed 47 instead of displaying the rotation instructing information of the bed 47 on the examination-procedure display unit 12c of the display unit 12, like the case of the right lateral decubitus position.

In this way, by causing the capsule endoscope 3 in the stomach to sequentially capture the in-vivo images, while changing the field of view, the in-vivo images of the stomach of the subject 1 can be captured substantially over the entire stomach, and as a result, the inside of the stomach of the subject 1 can be observed comprehensively. The posture display described above is only an example, and the posture instruction, the determination method of the bed drive control, and instruction contents are not limited to those described above. Further, in the modified example 2, posture information (a posture image or speech information instructing the posture), which is an example of examination procedure information, can be output by the examination-procedure display unit 12c or the notifying unit 34 to instruct the posture to be taken by the subject 1 to outside, similarly to any one of the first to third embodiments.

In the first to fourth embodiments and the modified examples of the present invention, the communication unit 13 of the display device according to the present invention and the communication unit 4b of the receiver 4 wirelessly communicate with each other to transfer various pieces of information such as the in-vivo images of the subject 1, but not limited to this, the communication unit 13 of the display device and the communication unit 4b of the receiver 4 may perform wire communication via a cable to transfer various pieces of information such as the in-vivo images of the subject 1. However, when it is taken into consideration to ensure an insulating state between the display device and the receiver 4, it is preferable to perform the wireless communication between the communication unit 13 of the display device and the communication unit 4b of the receiver 4. Further, transfer of the various pieces of information between the display device and the receiver 4 may be performed using a portable recording medium.

Further, in the first to fourth embodiments and the modified examples of the present invention, the position image indicating the intra-organ reached position of the capsule endoscope 3 is displayed on the position display unit 12b, and the posture image indicating the posture to be taken by the subject 1 corresponding to the intra-organ reached position is displayed on the examination-procedure display unit 12c. Alternatively, character information indicating the intra-organ reached position may be displayed on the position display unit 12b, or character information indicating the posture to be taken by the subject 1 may be displayed on the examination-procedure display unit 12c. That is, the position information to be displayed on the position display unit 12b can be any one of the image, the character, and a combination of these. Further, the posture information to be displayed on the examination-procedure display unit 12c can be any one of the image, the character, and a combination of these.

Further, in the first to fourth embodiments and the modified examples of the present invention, when the intra-organ reached position of the capsule endoscope 3 is in the predetermined internal organ such as the observed region, the position information indicating the intra-organ reached position is displayed on the position display unit 12b. Alternatively, when a capsule position is calculated, the position information indicating the intra-organ reached position corresponding to the calculated capsule position may be displayed on the position display unit 12b in each case, regardless of the position in the internal organs.

Further, in the first to fourth embodiments and the modified examples of the present invention, the capsule position is calculated based on the received field strength information acquired together with the in-vivo images. Alternatively, the position-related information of the capsule endoscope 3 to be used for calculating the capsule position may be intensity information of a magnetic field generated by the capsule endoscope 3, intensity information of an induction field, or X-ray image information acquired by imaging the inside of the subject 1 with X-rays, other than the received field strength information. In this case, a magnetism generating unit such as a permanent magnet or electromagnet can be incorporated in a casing of the capsule endoscope 3, and the intra-organ reached position of the capsule endoscope 3 in the subject 1 can be calculated based on the intensity of the magnetic field generated by the magnetism generating unit. Further, an LC marker can be incorporated in the casing of the capsule endoscope 3, and the intra-organ reached position of the capsule endoscope 3 in the subject 1 can be calculated based on the intensity of the induction field generated by the LC marker. Alternatively, by using an X-ray imaging device that images the subject 1 who has the capsule endoscope 3 in his internal organ with X-rays, the intra-organ reached position of the capsule endoscope 3 can be calculated based on images of the inside of the subject 1 captured by the X-ray imaging device. The control unit of the display device according to the present invention only needs to acquire the position-related information of the capsule endoscope 3 together with the in-vivo images.

Further, in the first to third embodiments and the modified examples of the present invention, the position information indicating the intra-organ reached position, the posture information indicating the posture to be taken by the subject 1, and the in-vivo images of the subject 1 are displayed on the display unit 12. However, at least the posture information of the subject 1 needs only to be displayed on the display unit 12, and it is preferable to further display at least one of the position information and the in-vivo images.

In the fourth embodiment of the present invention, the posture information indicating the posture to be taken by the subject 1 is displayed on the display unit 12. Alternatively, at least one of the position information indicating the intra-organ reached position, the posture information indicating the posture to be taken by the subject 1, and the in-vivo images of the subject 1 may be displayed on the display unit 12.

Further, in the second to fourth embodiments and the modified examples of the present invention, when the stagnant state of the capsule continues for a predetermined time or longer, the check window 22a is displayed on the display unit 12, to check a posture change instruction of the subject 1. However, the check window 22a may not be displayed. In this case, every time the stagnant state of the capsule continues for a predetermined time or longer, the posture to be taken by the subject 1 corresponding to the intra-organ reached position of the capsule endoscope 3 is determined.

In the third and fourth embodiments of the present invention, every time the in-vivo image of the subject 1 is acquired, the position of the capsule endoscope 3 that captures the in-vivo image (that is, the capsule position in the subject 1) is calculated. However, it can be determined whether the stagnant state of the capsule continues for a predetermined time or longer based on the position-related information of the capsule endoscope 3 acquired together with the in-vivo image, and when it is determined that the stagnant state of the capsule continues for a predetermined time or longer, the capsule position can be calculated in each case. In this case, the control unit of the display device according to the third and fourth embodiments can calculate the capsule position when the stagnant state of the capsule continues for a predetermined time or longer and there is the posture change instruction of the subject 1, like the control unit 28 in the display device 27 according to the modified example of the second embodiment.

Further, in the first to fourth embodiments and the modified examples of the present invention, the posture to be taken by the subject 1 corresponding to the ascending colon is determined as the Trendelenburg's position, the posture to be taken by the subject 1 corresponding to the transverse colon is determined as the left lateral decubitus position, and the posture to be taken by the subject 1 corresponding to the descending colon is determined as the sitting position. However, the posture to be taken by the subject 1 corresponding to the intra-organ reached position of the capsule endoscope 3 can be a desired posture such as the lower body elevated posture, the right side elevated posture, and the upper body elevated posture, so long as the posture accelerates the advancement of the capsule endoscope 3 inside the internal organs (or obstructs the stagnant state).

Further, in the first to fourth embodiments and the modified examples of the present invention, when the intra-organ reached position of the capsule endoscope 3 is a position inside the large intestine of the subject 1, the posture to be taken by the subject 1 is determined. However, when the intra-organ reached position of the capsule endoscope 3 is a position in a desired region other than large intestine, for example, stomach or small intestine, the posture to be taken by the subject 1 can be determined.

According to the above-described embodiments of the present invention, a display device that can sequentially display a posture of a subject, which accelerates advancement of a capsule endoscope inside the subject corresponding to a position of the capsule endoscope in internal organs where it has reached, and can support smooth advancement of the capsule endoscope having reached inside of a desired internal organ such as large intestine, and an in-vivo information acquiring system using the display device can be achieved.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A display device comprising:
    a display unit that displays examination procedure information indicating an examination procedure of a subject; and
    a control unit that acquires position related information of a capsule endoscope inserted into the subject, calculates a position of the capsule endoscope based on the acquired position-related information, determines a to-be-executed examination procedure of the subject corresponding to the calculated position, and performs control to display the examination procedure information indicating the determined to-be-executed examination procedure of the subject,
    wherein the examination procedure information is posture information indicating a posture to be taken by the subject, and the control unit determines whether the capsule endoscope is in a stagnant state based on the calculated position of the capsule endoscope, determines the posture to be taken by the subject when the stagnant state continues for a predetermined time or longer and when the position of the capsule endoscope is a predetermined reached position, and performs control to display the posture information indicating the determined posture to be taken by the subject.

2. The display device according to claim 1, further comprising an input unit that inputs an instruction indicating whether to change the posture of the subject, wherein the display unit displays a request screen for requesting an input of the instruction whether to change the posture of the subject, and the control unit performs control to display the request screen when the stagnant state continues for the predetermined time or longer, determines the posture to be taken by the subject when the input unit inputs a posture change instruction of the subject and when the position of the capsule endoscope is the predetermined reached position, and performs control to display the posture information indicating the determined posture to be taken by the subject.

3. The display device according to claim 1, further comprising a notifying unit that notifies of speech information indicating the posture of the subject, wherein the control unit performs control to notify of the speech information corresponding to the posture to be taken by the subject indicated by the posture information.

4. The display device according to claim 1, wherein the control unit specifies a reached position in the subject of the capsule endoscope based on the calculated position of the capsule endoscope, and controls the display unit to display position information indicating the specified reached position in the subject.

5. The display device according to claim 1, wherein the control unit acquires in-vivo images captured by the capsule endoscope and controls the display unit to display the acquired in-vivo images.

6. A display device comprising:
a display unit that displays examination procedure information indicating an examination procedure of a subject; and
a control unit that acquires position-related information of a capsule endoscope inserted into the subject, calculates a position of the capsule endoscope based on the acquired position-related information, determines a to-be-executed examination procedure of the subject corresponding to the calculated position, and performs control to display the examination procedure information indicating the determined to-be-executed examination procedure of the subject,
wherein the examination procedure information is posture information indicating a posture to be taken by the subject, and
the control unit determines whether the capsule endoscope is in a stagnant state based on the acquired position-related information, calculates a position of the capsule endoscope based on the acquired position-related information when the stagnant state continues for a predetermined time or longer, determines the posture to be taken by the subject corresponding to the calculated position, and performs control to display the posture information indicating the determined posture to be taken by the subject.

7. The display device according to claim 6, wherein when the stagnant state continues for the predetermined time or longer and when the position of the capsule endoscope is a predetermined reached position, the control unit determines the posture to be taken by the subject and performs control to display the posture information indicating the determined posture to be taken by the subject.

8. The display device according to claim 6, further comprising an input unit that inputs an instruction indicating whether to change the posture of the subject, wherein the display unit displays a request screen for requesting an input of the instruction whether to change the posture of the subject, and the control unit performs control to display the request screen when the stagnant state continues for the predetermined time or longer, determines the posture to be taken by the subject when the input unit inputs a posture change instruction of the subject and when the position of the capsule endoscope is the predetermined reached position, and performs control to display the posture information indicating the determined posture to be taken by the subject.

9. An in-vivo information acquiring system comprising:
a mounting unit that has a subject mounted thereon;
a driving unit that drives the mounting unit to change a posture of the subject;
a receiver that receives in-vivo images captured by a capsule endoscope inserted into the subject and position-related information of the capsule endoscope; and
a display device that acquires the in-vivo images and displays the acquired in-viva images, wherein
the display device includes a control unit that acquires the position-related information, calculates a position of the capsule endoscope based on the acquired position-related information, determines a posture to be taken by the subject corresponding to the calculated position, and performs drive control of the driving unit to change the posture of the subject according to the determined posture to be taken by the subject, and
the control unit determines whether the capsule endoscope is in a stagnant state based on the calculated position of the capsule endoscope, determines the posture to be taken by the subject when the stagnant state continues for a predetermined time or longer and when the position of the capsule endoscope is a predetermined reached position, and performs drive control of the driving unit to change the posture of the subject according to the determined posture to be taken by the subject.

10. The in-vivo information acquiring system according to claim 9, wherein the control unit specifies a reached position in the subject of the capsule endoscope based on the calculated position of the capsule endoscope and controls the display device to display position information indicating the specified reached position in the subject.

11. An in-vivo information acquiring system comprising:
a mounting unit that has a subject mounted thereon;
a driving unit that drives the mounting unit to change a posture of the subject;
a receiver that receives in-vivo images captured by a capsule endoscope inserted into the subject and position-related information of the capsule endoscope; and
a display device that acquires the in-vivo images and displays the acquired in-vivo images, wherein
the display device includes a control unit that acquires the position-related information, calculates a position of the capsule endoscope based on the acquired position-related information, determines a posture to be taken by the subject corresponding to the calculated position, and performs drive control of the driving unit to change the posture of the subject according to the determined posture to be taken by the subject, and the control unit determines whether the capsule endoscope is in a stagnant state based on the acquired position-related information of the capsule endoscope, calculates a position of the capsule endoscope based on the acquired position-related information when the stagnant state continues for a predetermined time or longer, determines the posture to be taken by the subject corresponding to the calculated position, and performs drive control of the driving unit to change the posture of the subject according to the determined posture to be taken by the subject.

12. The in-vivo information acquiring system according to claim 11, wherein the control unit determines the posture to be taken by the subject when the stagnant state continues for the predetermined time or longer and when the position of the capsule endoscope is a predetermined reached position, and performs drive control of the driving unit to change the posture of the subject according to the determined posture to be taken by the subject.

13. A display method for displaying examination procedure information indicating an examination procedure of a subject, the method comprising:

acquiring position-related information of a capsule endoscope inserted into the subject;

calculating a position of the capsule endoscope based on the acquired position-related information;

determining a to-be-executed examination procedure of the subject corresponding to the calculated position; and performing control to display the examination procedure information indicating the determined to-be-executed examination procedure of the subject, wherein the examination procedure information is posture information indicating a posture to be taken by the subject, and the method further comprising:

determining whether the capsule endoscope is in a stagnant state, wherein when the stagnant state continues for a predetermined time or longer and when the position of the capsule endoscope is a predetermined reached position, the determining and the performing are carried out.

* * * * *